(12) United States Patent
Beckman et al.

(10) Patent No.: US 12,029,515 B2
(45) Date of Patent: Jul. 9, 2024

(54) SURGICAL TOOLS WITH PROXIMALLY MOUNTED, CABLE BASED ACTUATION SYSTEMS

(71) Applicant: Cilag GmbH International, Zug (CH)

(72) Inventors: Andrew T. Beckman, Cincinnati, OH (US); Charles J. Scheib, Loveland, OH (US); Benjamin D. Dickerson, San Francisco, CA (US); Jason Alan Hill, Loveland, OH (US)

(73) Assignee: Cilag GmbH International, Zug (CH)

( * ) Notice: Subject to any disclaimer, the term of this patent is extended or adjusted under 35 U.S.C. 154(b) by 818 days.

(21) Appl. No.: 17/153,239

(22) Filed: Jan. 20, 2021

(65) Prior Publication Data

US 2022/0226054 A1    Jul. 21, 2022

(51) Int. Cl.
*A61B 34/37*    (2016.01)
*A61B 17/068*   (2006.01)
*A61B 17/3201*  (2006.01)
*A61B 34/00*    (2016.01)
*A61B 17/29*    (2006.01)
*A61B 34/30*    (2016.01)

(52) U.S. Cl.
CPC ............ *A61B 34/37* (2016.02); *A61B 17/068* (2013.01); *A61B 17/3201* (2013.01); *A61B 34/71* (2016.02); *A61B 17/29* (2013.01); *A61B 2034/302* (2016.02); *A61B 2034/305* (2016.02); *A61B 2034/715* (2016.02)

(58) Field of Classification Search
CPC ... A61B 34/37; A61B 17/068; A61B 17/3201; A61B 34/71; A61B 17/29; A61B 2034/302; A61B 2034/305; A61B 2034/715
See application file for complete search history.

(56) References Cited

U.S. PATENT DOCUMENTS

| | | | |
|---|---|---|---|
| 6,817,974 B2* | 11/2004 | Cooper | A61B 17/00234 606/205 |
| 9,889,568 B2* | 2/2018 | Kilroy | A61B 34/71 |
| 10,383,699 B2* | 8/2019 | Kilroy | A61B 34/25 |
| 2021/0015572 A1 | 1/2021 | Gomez et al. | |
| 2021/0022815 A1 | 1/2021 | Abbott | |

* cited by examiner

*Primary Examiner* — Julian W Woo
(74) *Attorney, Agent, or Firm* — Vorys, Sater, Seymour and Pease LLP

(57) ABSTRACT

A robotic surgical tool includes an elongate shaft extendable through a handle that provides a drive input, an actuation system housed within the handle and operatively coupled to the drive input such that actuation of the drive input operates the actuation system, a rocker bar system arranged at a proximal end of the shaft and actuatable to articulate an end effector at a distal end of the shaft, and first and second drive cables extending along a portion of the shaft, each drive cable having a proximal end anchored to the shaft proximal to the handle and a distal end anchored to the shaft distal to the handle, wherein the drive cables are threaded through portions of the actuation and rocker bar systems such that operation of the actuation system acts on the drive cables and thereby actuates the rocker bar system to articulate the end effector.

20 Claims, 20 Drawing Sheets

SURGICAL TOOLS WITH PROXIMALLY MOUNTED, CABLE BASED ACTUATION SYSTEMS

TECHNICAL FIELD

The systems and methods disclosed herein are directed to robotic surgical tools and, more particularly to, surgical tools with proximally mounted, cable-based actuation systems that operate distally mounted end effectors.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving drive cables, rods, and/or other mechanical mechanisms causes the end effector to articulate to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes an elongate shaft extendable through a handle that provides a drive input, an actuation system housed within the handle and operatively coupled to the drive input such that actuation of the drive input operates the actuation system, a rocker bar system arranged at a proximal end of the shaft and actuatable to articulate an end effector at a distal end of the shaft, and first and second drive cables extending along a portion of the shaft, each drive cable having a proximal end anchored to the shaft proximal to the handle and a distal end anchored to the shaft distal to the handle, wherein the first and second drive cables are threaded through portions of the actuation and rocker bar systems such that operation of the actuation system acts on the first and second drive cables and thereby actuates the rocker bar system to articulate the end effector. In a further embodiment, the robotic surgical further includes an instrument driver arranged at an end of a robotic arm and matable with the handle, wherein the instrument driver provides a drive output matable with the drive input, and wherein the shaft extends through the instrument driver via a central aperture defined longitudinally through the instrument driver. In another further embodiment, the actuation system comprises a lead screw extending from the drive input and rotatable therewith, a nut threadably mounted to the lead screw such that rotation of the lead screw causes the nut to traverse the lead screw, a first pulley rotatably mounted to an armature extending laterally from the nut, a second pulley rotatably coupled to the handle and axially offset from the first pulley, wherein movement of the nut along the lead screw moves the first pulley toward or away from the second pulley, and first and second idler pulleys rotatably coupled to the handle and longitudinally spaced from each other, wherein the first drive cable is guided through the first and second pulleys and the first and second idler pulleys, and wherein the second drive cable is guided through the first and second pulleys. In another further embodiment, the first idler pulley is mounted within the handle at or above a proximal end of external threading of the lead screw, and wherein the second idler pulley is mounted within the handle at or below a distal end of the external threading. In another further embodiment, the nut defines one or more channel guides engageable with one or more opposing guide structures provided by the handle, and wherein receiving the one or more opposing guide structures in the one or more channel guides prevents the nut from rotating as the lead screw rotates. In another further embodiment, proximal movement of one unit of length of the nut along the lead screw results in one or more units of length of the first drive cable being paid out from the actuation system to the shaft, and one or more units of length of the second drive cable being paid in to the actuation system from the shaft, and wherein distal movement of one unit of length of the nut along the lead screw results in one or more units of length of the second drive cable being paid out from the actuation system to the shaft, and one or more units of length of the first drive cable being paid in to the actuation system from the shaft. In another further embodiment, the rocker bar system comprises a rocker bar pivotably mounted at the proximal end of the shaft and providing first and second lateral arms, wherein the first and second drive cables terminate at the rocker bar, and first and second drive rods pivotably coupled to the first and second lateral arms, respectively, and extending longitudinally to a wrist that interposes the distal end of the shaft and the end effector, wherein antagonistic movement of the first and second drive cables caused by operation of the actuation system causes the rocker bar to pivot and thereby antagonistically operate the first and second drive rods at the wrist to articulate the end effector. In another further embodiment, the rocker bar system further comprises a tail piece coupled to the proximal end of the shaft, first and second rocker pulleys rotatably mounted to the first and second lateral arms, respectively, and receiving the first and second drive cables, respectively, a first redirection pulley rotatably mounted to the tail piece and redirecting the first drive cable to the first rocker pulley, and a second redirection pulley rotatably mounted to the tail piece and redirecting the second drive cable to the second rocker pulley. In another further embodiment, the robotic surgical tool further includes one or more first additional pulleys arranged between the first redirection pulley and the first rocker pulley, and one or more second additional pulleys arranged between the second redirection pulley and the second rocker pulley. In another further embodiment, the rocker bar system further comprises a yoke coupled to the proximal end of the shaft, and wherein the rocker bar is pivotably mounted to the yoke at a pin defined by the yoke. In another further embodiment, the end effector is selected from the group consisting of a surgical stapler, a tissue grasper, surgical scissors, an advanced energy vessel sealer, a clip applier, a needle driver, a babcock including a pair of opposed grasping jaws, bipolar jaws, and any combination thereof.

Embodiments disclosed herein also include a method of operating a robotic surgical tool including actuating a drive input of a robotic surgical tool, the robotic surgical tool having an elongate shaft extending through a handle that provides the drive input, an actuation system housed within the handle and operatively coupled to the drive input, a rocker bar system arranged at a proximal end of the shaft, and first and second drive cables extending along a portion of the shaft and threaded through portions of the actuation and rocker bar systems, each drive cable having a proximal end anchored to the shaft proximal to the handle and a distal end anchored to the shaft distal to the handle. The method further includes operating the actuation system by actuating the drive input and thereby antagonistically moving the first and second drive cables along the shaft, actuating the rocker bar system with the first and second drive cables and thereby antagonistically moving first and second drive rods extending to a wrist arranged at a distal end of the shaft, and articulating an end effector coupled to the wrist with antagonistic movement of the first and second drive rods. In a further embodiment, the handle is matable with an instrument driver arranged at an end of a robotic arm and the instrument driver provides a drive output, and wherein actuating the drive input comprises actuating the drive output mated with the drive input. In another further embodiment, the actuation system comprises a lead screw extending from the drive input, a nut threadably mounted to the lead screw, a first pulley rotatably mounted to an armature extending from the nut, a second pulley rotatably coupled to the handle and axially offset from the first pulley, and first and second idler pulleys rotatably coupled to the handle and longitudinally spaced from each other, and wherein operating the actuation system comprises rotating the lead screw as the drive input rotates, and moving the nut along the lead screw as the lead screw rotates and thereby moving the first pulley toward or away from the second pulley, wherein the first drive cable is guided through the first and second pulleys and the first and second idler pulleys, and wherein the second drive cable is guided through the first and second pulleys. In another further embodiment, the method further includes moving the nut proximally one unit of length along the lead screw and thereby paying out one or more units of length of the first drive cable from the actuation system to the shaft, and paying in one or more units of length of the second drive cable into the actuation system from the shaft, and moving the nut distally one unit of length along the lead screw and thereby paying out one or more units of length of the second drive cable from the actuation system to the shaft, and paying in one or more units of length of the first drive cable into the actuation system from the shaft. In another further embodiment, the rocker bar system includes a rocker bar pivotably mounted at the proximal end of the shaft and providing first and second lateral arms, the first and second drive rods being pivotably coupled to the first and second lateral arms, respectively and the first and second drive cables terminating at the rocker bar, and wherein antagonistically moving the first and second drive cables along the shaft comprises pivoting the rocker bar and thereby antagonistically operating the first and second drive rods at the wrist, and articulating the end effector with antagonistic movement of the first and second drive rods. In another further embodiment, the method further includes moving the shaft relative to the handle while simultaneously articulating the end effector.

Embodiments disclosed herein also include a robotic surgical tool that includes a shaft extended through a handle providing a drive input, an actuation mechanism housed within the handle and having a lead screw extending from the drive input and a nut threadably mounted to the lead screw such that rotation of the lead screw causes the nut to traverse the lead screw, a rocker bar pivotably mounted at a proximal end of the shaft and having first and second drive rods pivotably coupled to first and second lateral arms, respectively, of the rocker bar and extending longitudinally to a wrist arranged at a distal end of the shaft, and first and second drive cables extending along a portion of the shaft, each drive cable having a proximal end anchored to the shaft proximal to the handle and a distal end anchored to the shaft distal to the handle, wherein the first and second drive cables are threaded through portions of the actuation system and the rocker bar such that movement of the nut along the lead screw acts on the first and second drive cables and correspondingly causes the rocker bar to pivot and antagonistically operate the first and second drive rods to articulate an end effector operatively coupled to the wrist. In a further embodiment, the actuation system further includes a first pulley rotatably mounted to an armature extending laterally from the nut, a second pulley rotatably coupled to the handle and axially offset from the first pulley, wherein movement of the nut along the lead screw moves the first pulley toward or away from the second pulley, and first and second idler pulleys rotatably coupled to the handle and longitudinally spaced from each other, wherein the first drive cable is guided through the first and second pulleys and the first and second idler pulleys, and wherein the second drive cable is guided through the first and second pulleys. In another further embodiment, antagonistic movement of the first and second drive cables caused by operation of the actuation system causes the rocker bar to pivot and thereby antagonistically operate the first and second drive rods at the wrist to articulate the end effector.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
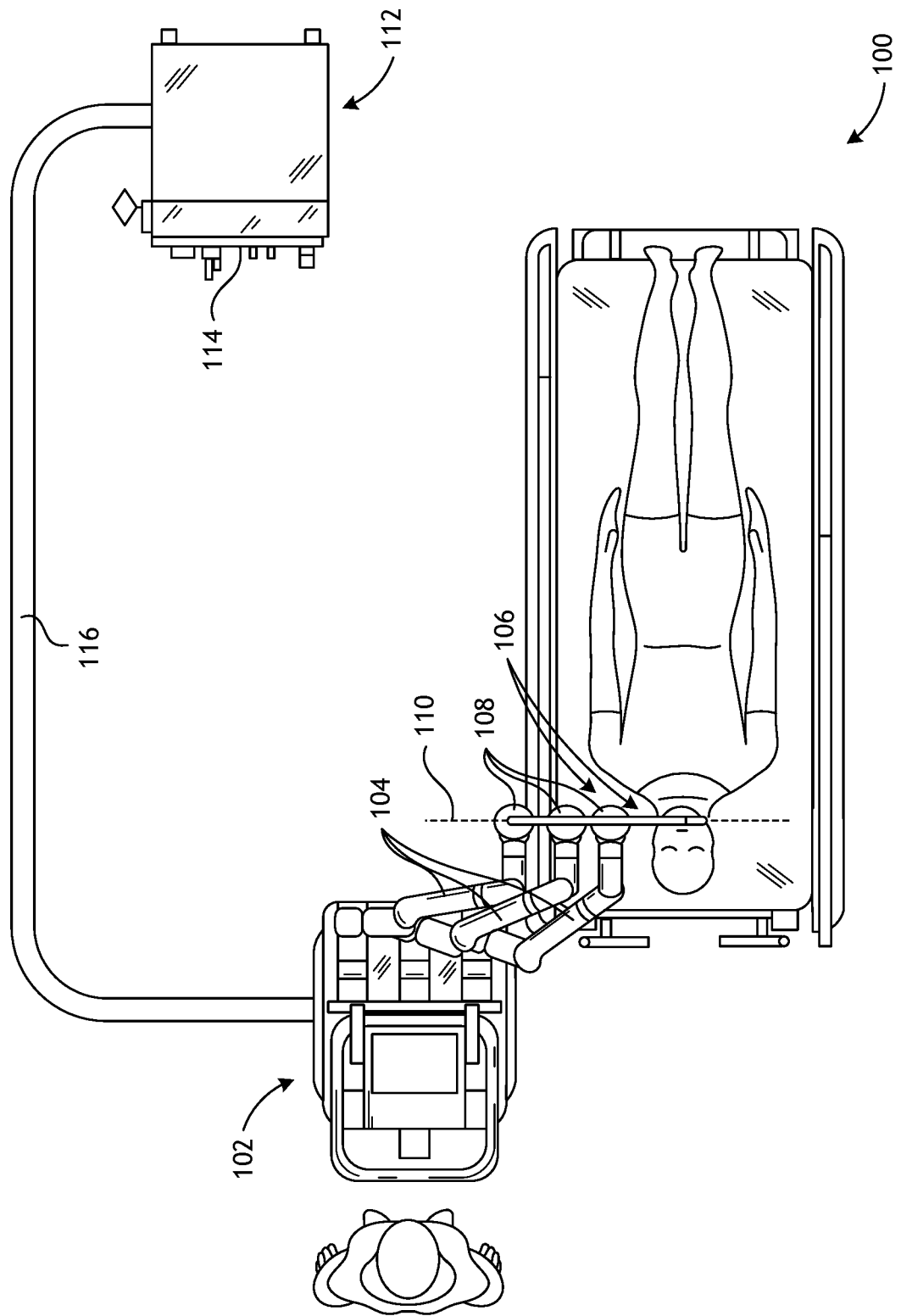
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastro-intestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
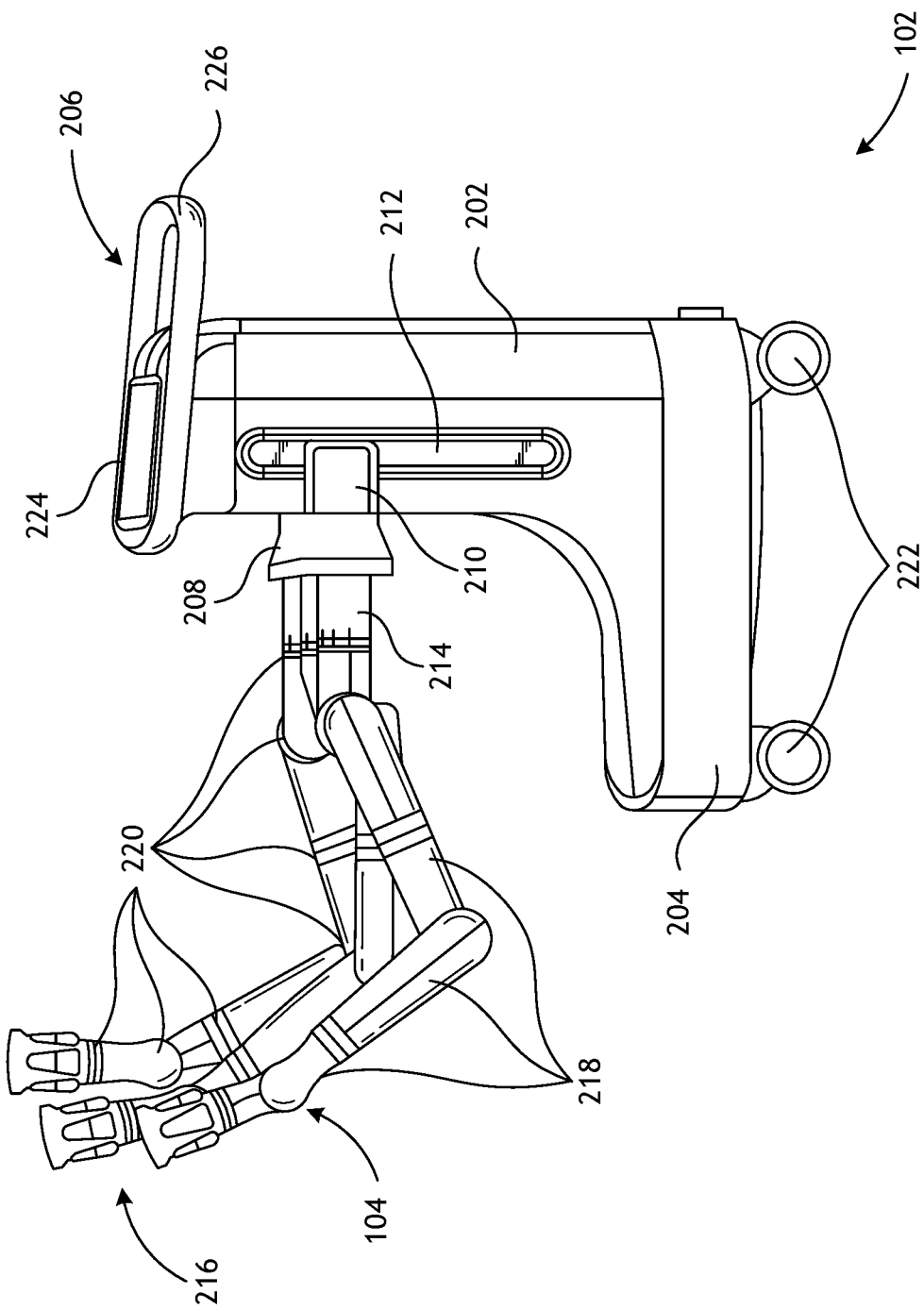
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
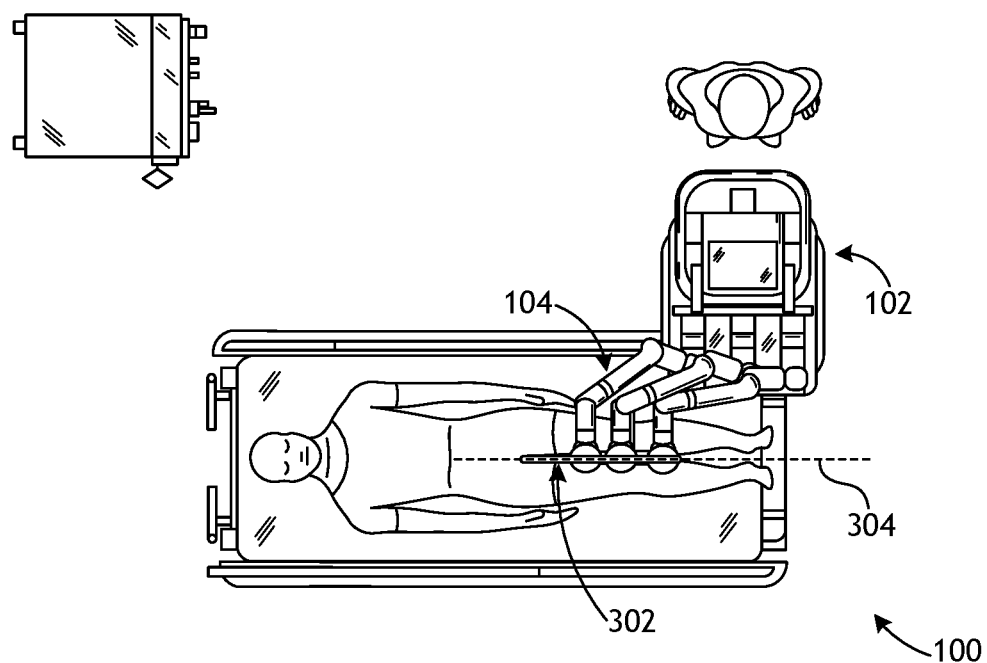
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
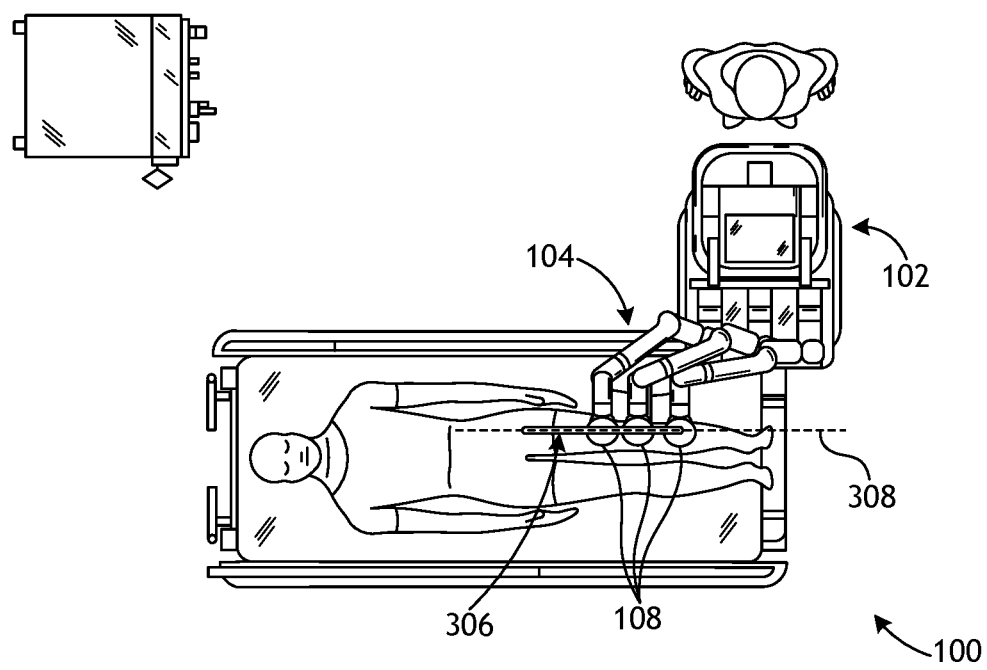
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
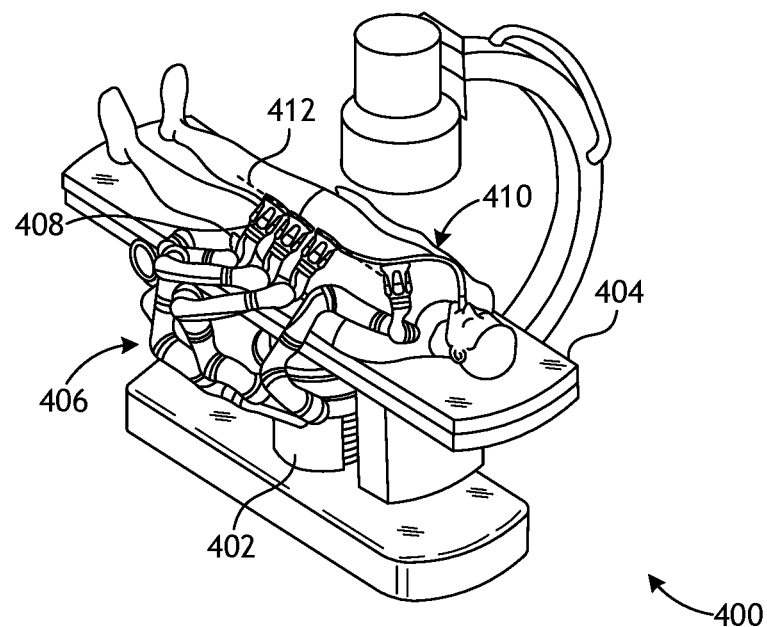
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
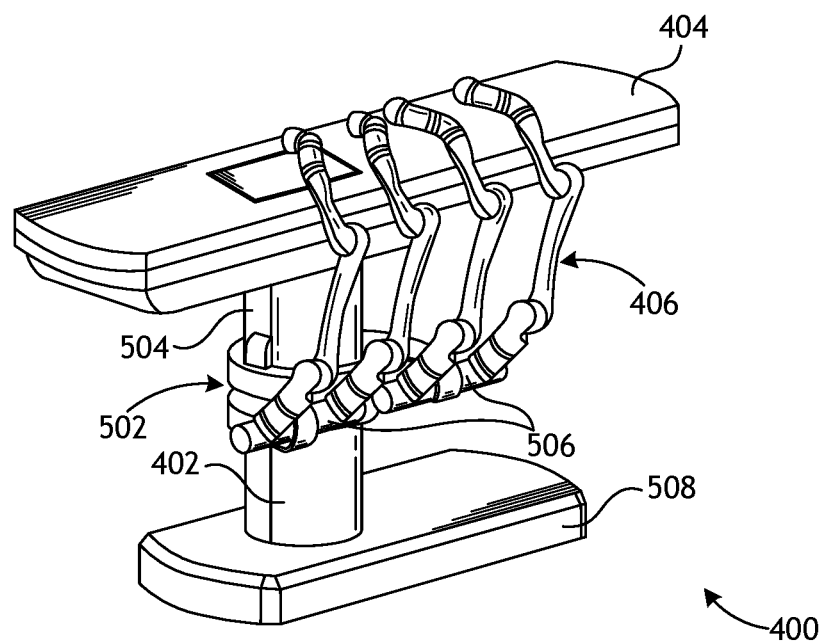
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
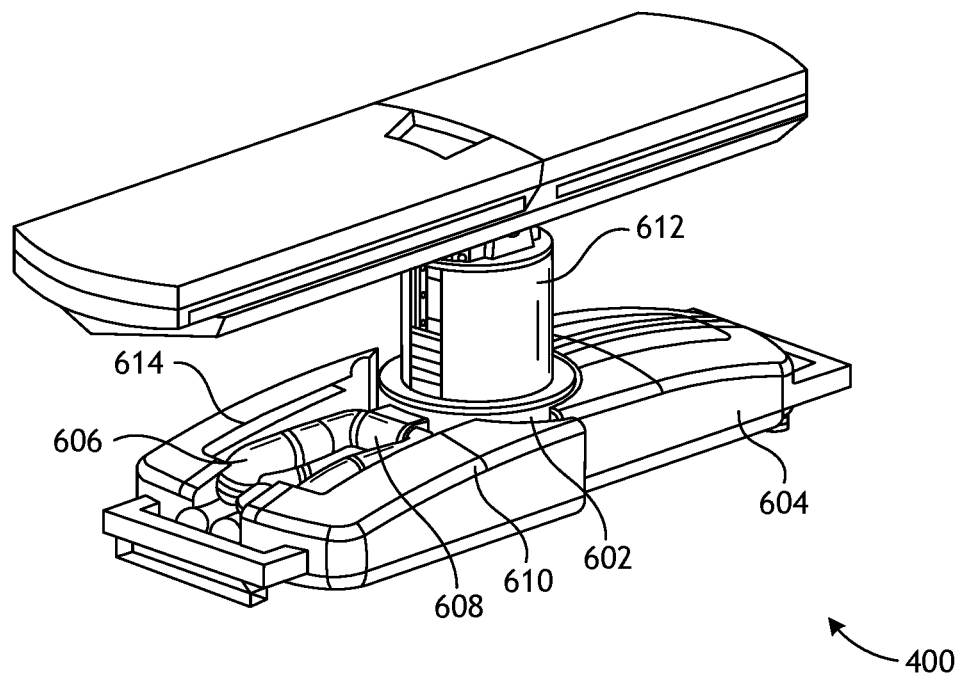
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
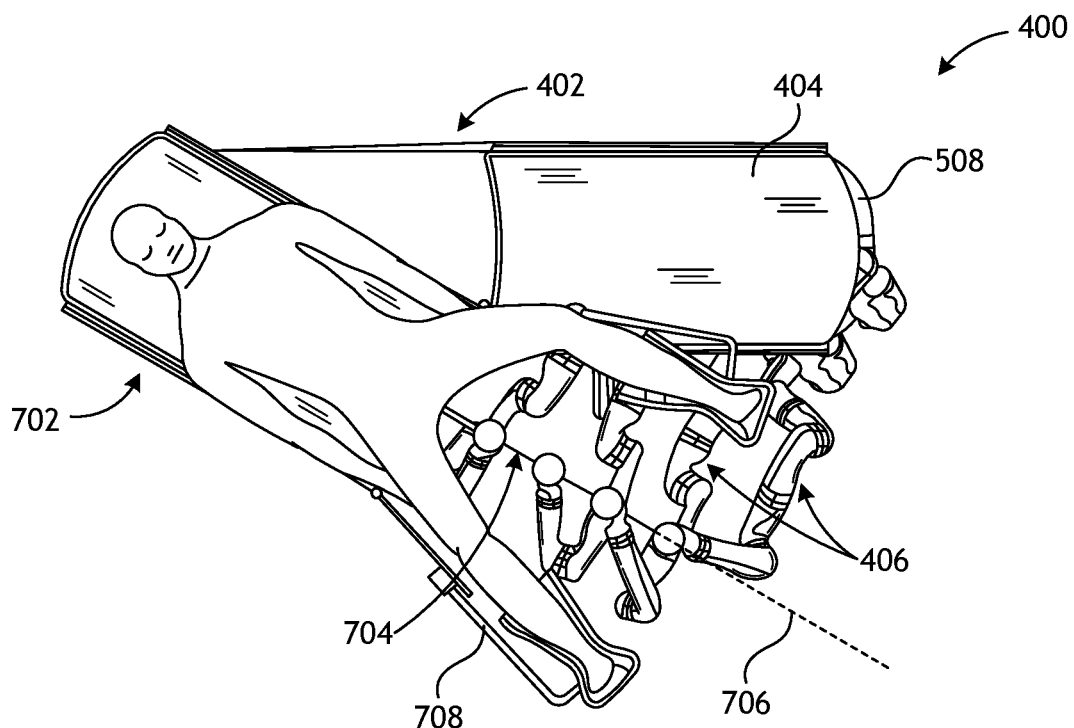
FIG. 7A illustrates an embodiment of a table-based robotic system configured for a ureteroscopy procedure.
Figure 7B:
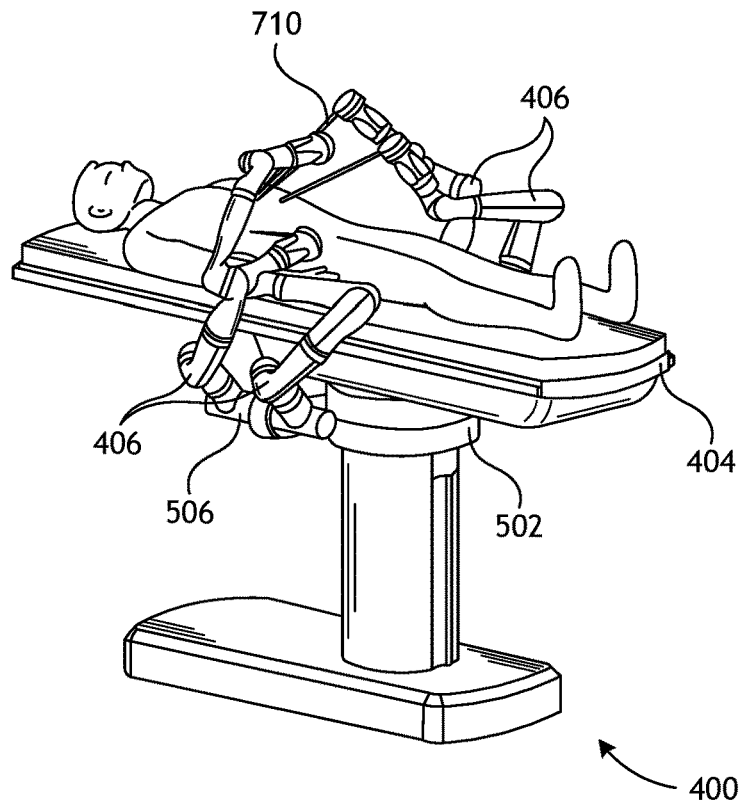
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
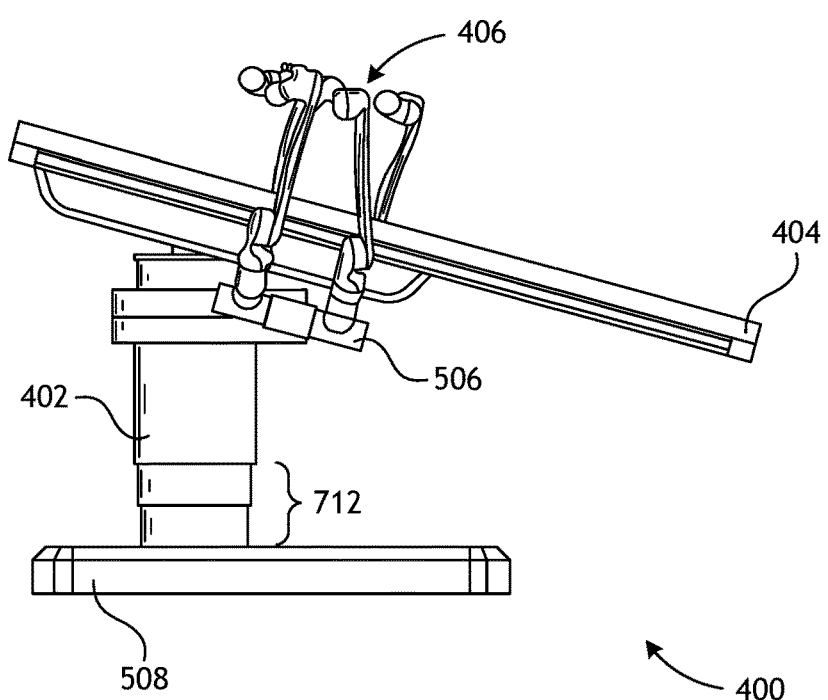
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
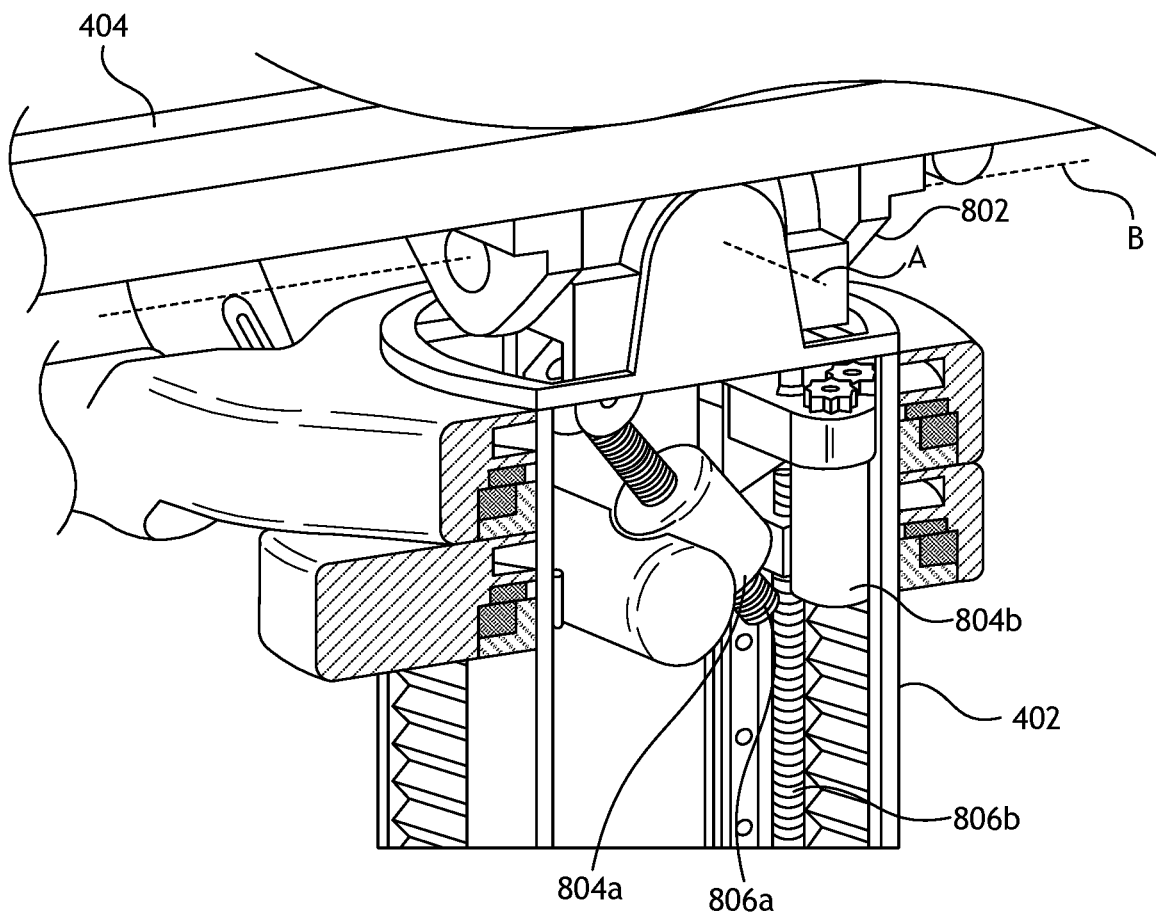
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
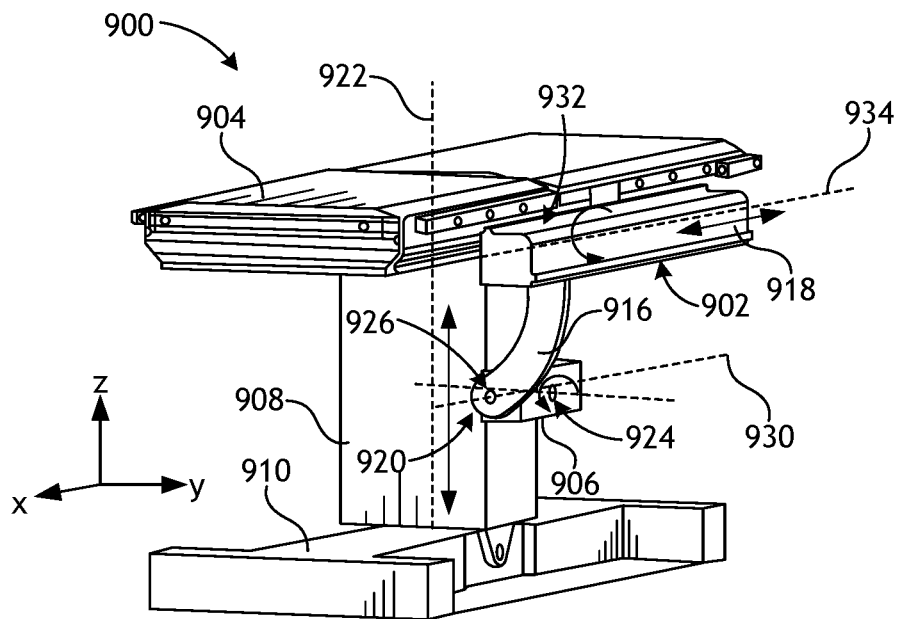
FIG. 9A illustrates an alternative embodiment of a table-based robotic system.
Figure 9B:
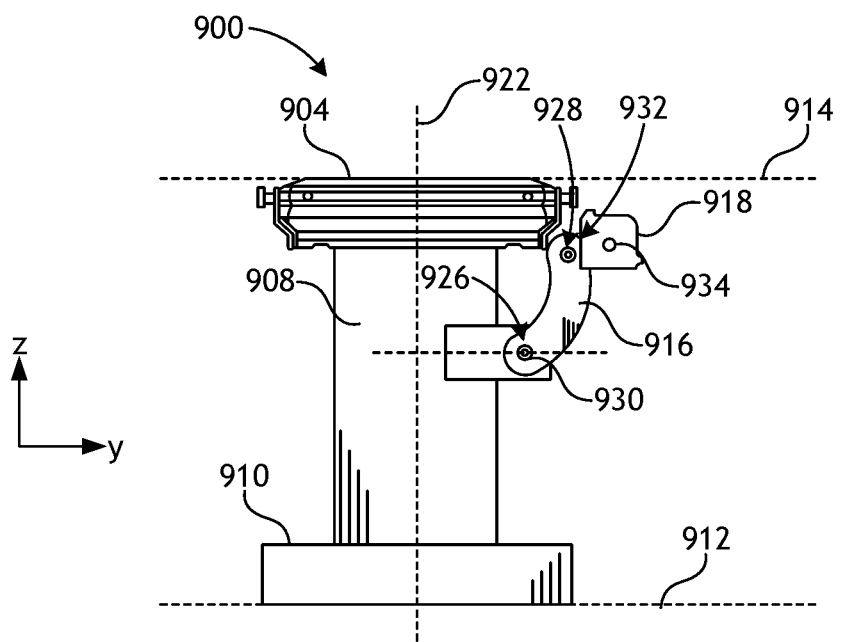
FIG. 9B illustrates an end view of the table-based robotic system of FIG.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
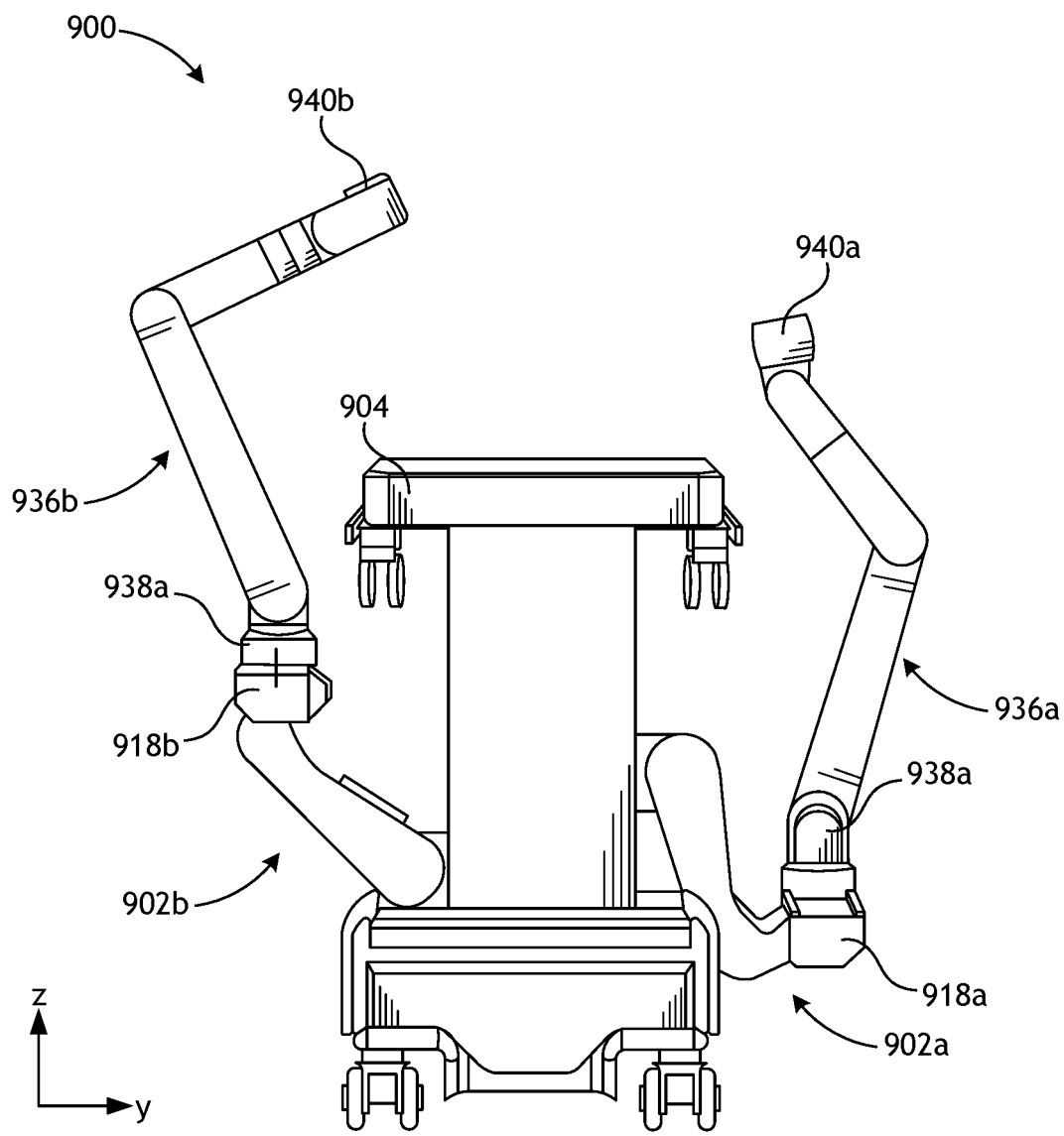
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
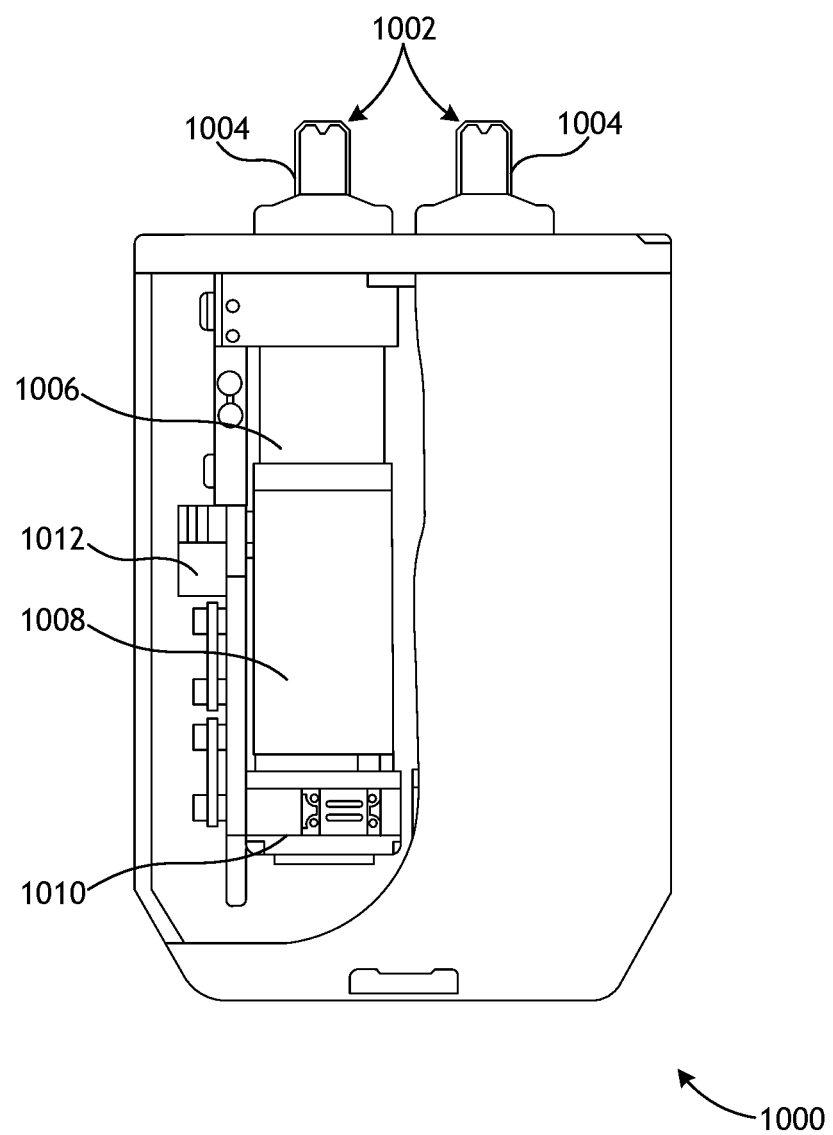
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
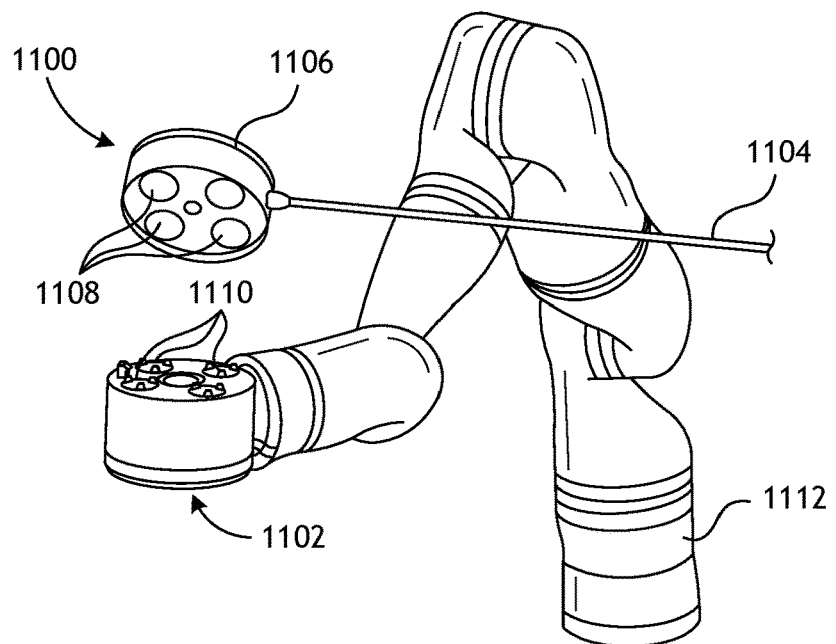
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
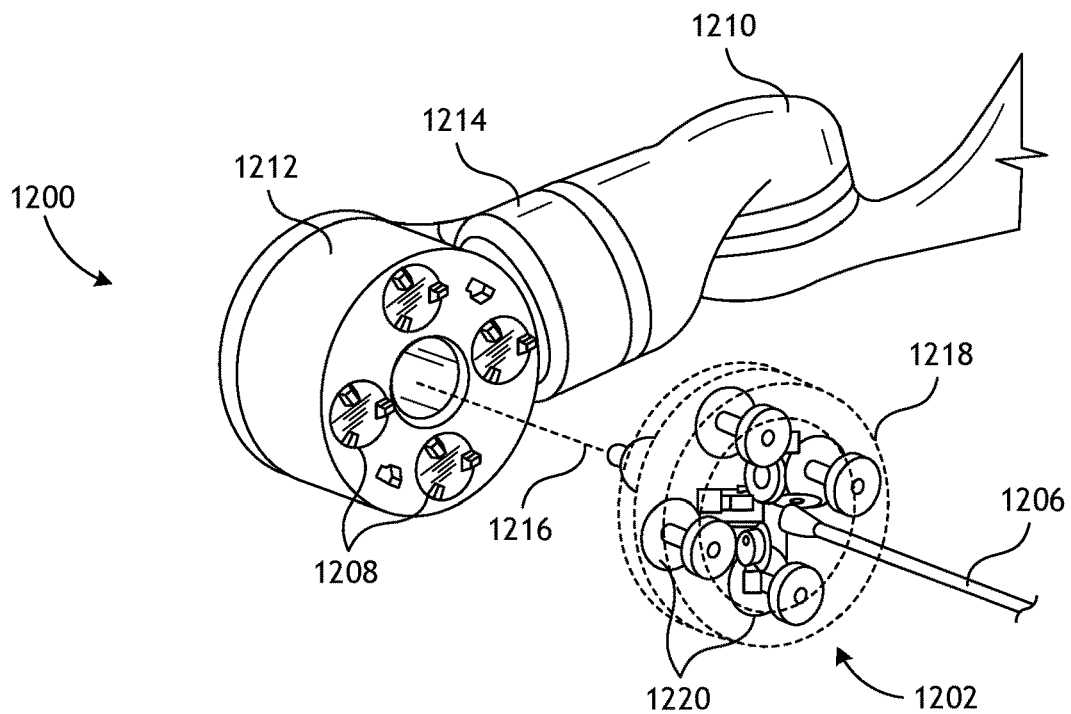
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
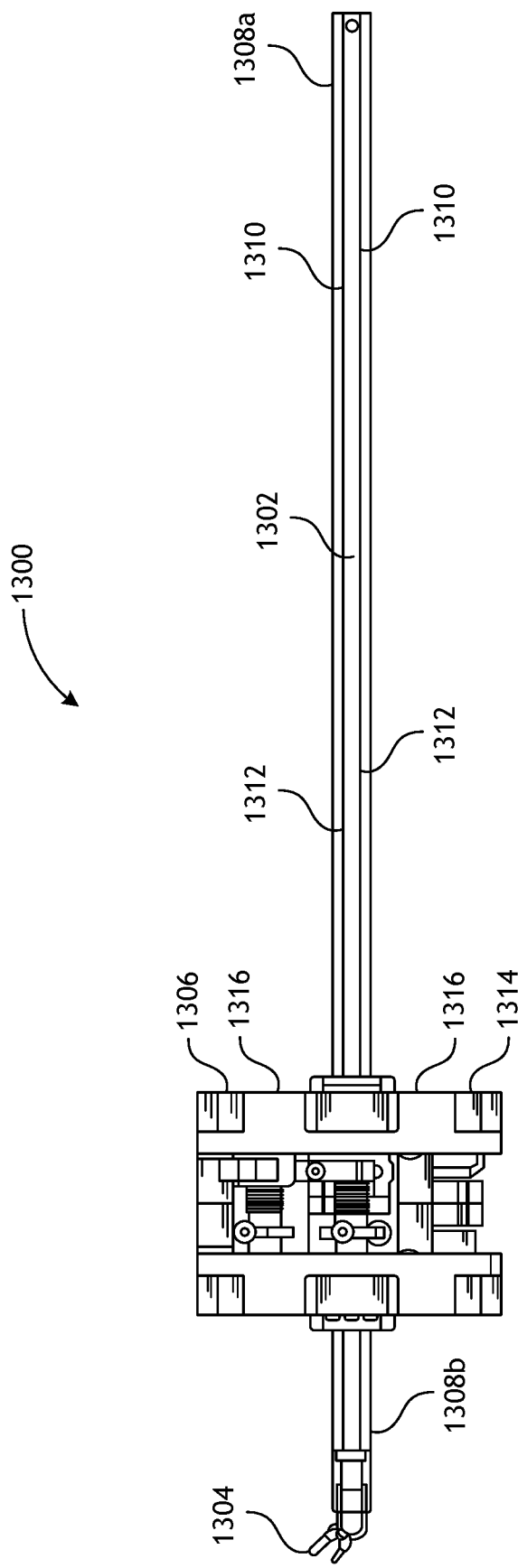
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
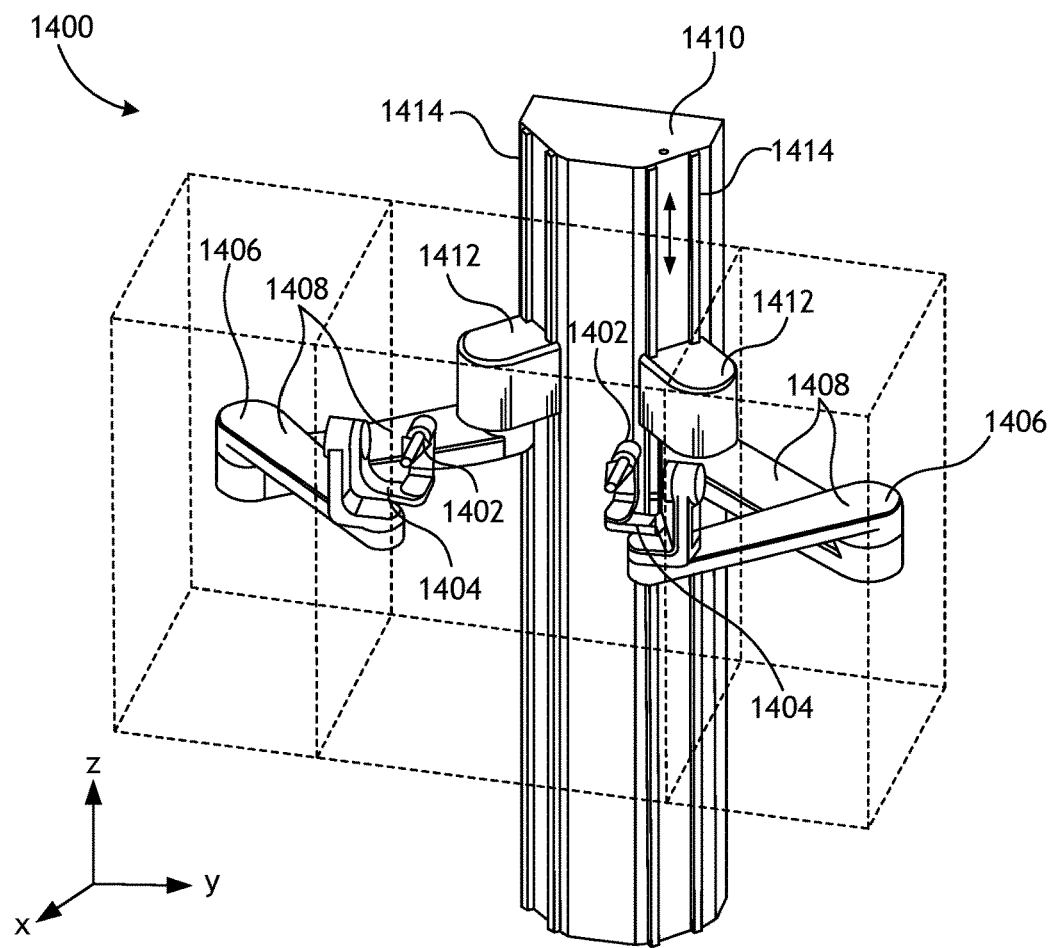
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
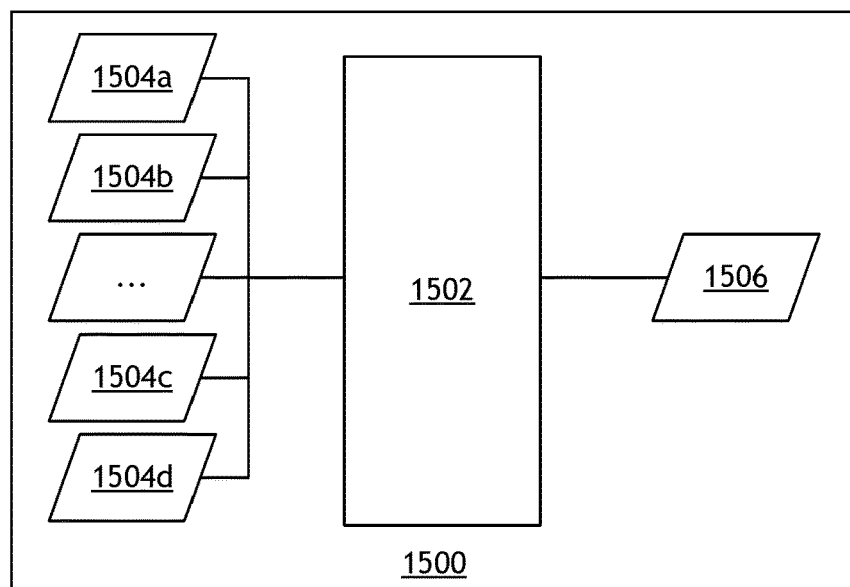
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504a-d in combination(s). In some cases, such a combination may use a probabilistic approach where the localization module 1502 assigns a confidence weight to the location determined from each of the input data 1504a-d. Thus, where the EM data 1504c may not be reliable (as may be the case where there is EM interference) the confidence of the location determined by the EM data 1504c can be decrease and the localization module 1502 may rely more heavily on the vision data 1504b and/or the robotic command and kinematics data 1504d.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description

Figure 16:
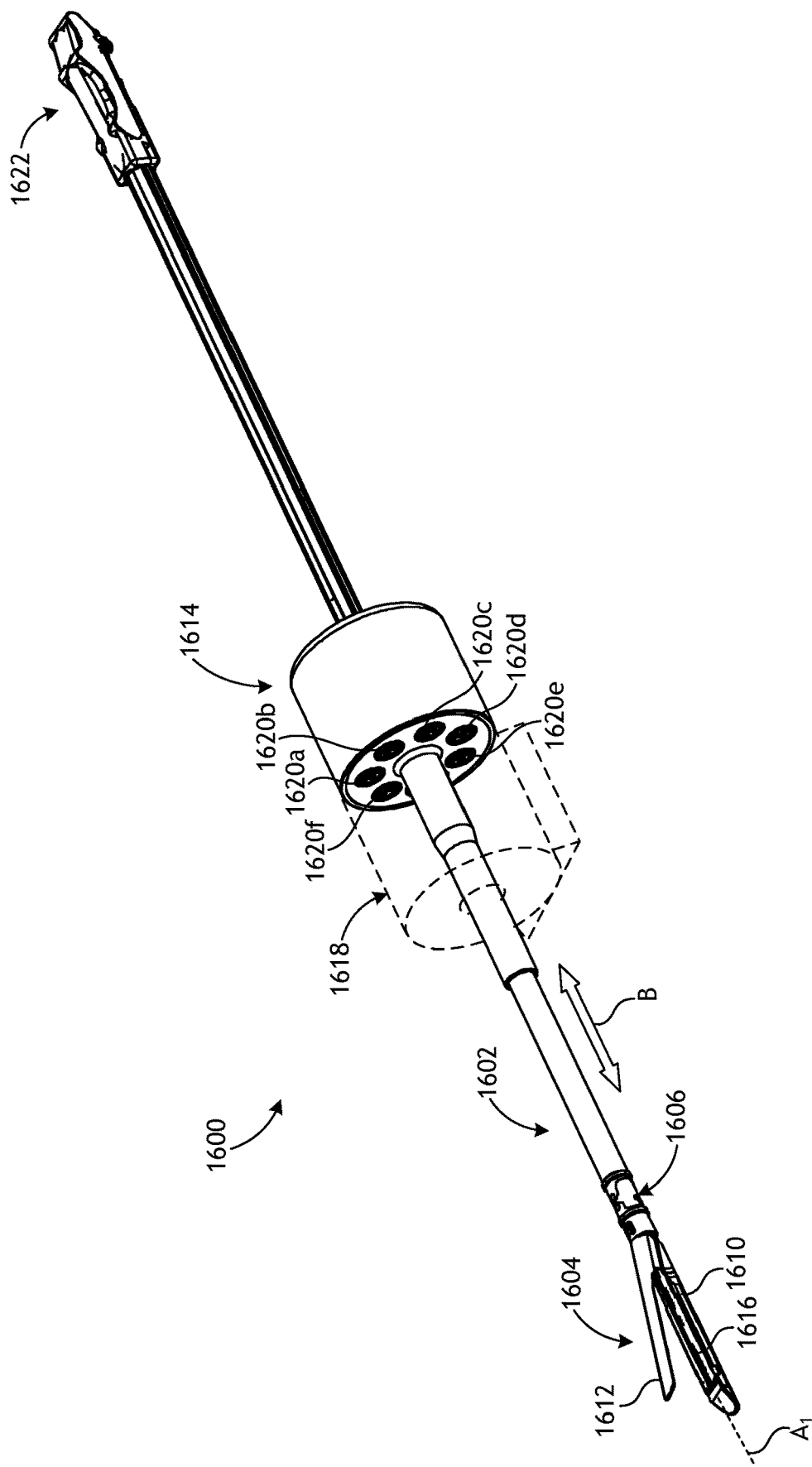
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to simultaneously cut and staple (fasten) tissue. As illustrated, the end effector 1604 includes opposing jaws 1610, 1612 configured to move (articulate) between open and closed positions. Alternatively, the end effector 1604 may comprise other types of instruments with opposing jaws such as, but not limited to, other types of surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods, such as a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 may be rotatable (pivotable) relative to the first jaw 1610 to actuate the end effector 1604 between an open, unclamped position and a closed, clamped position. In other embodiments, however, the first jaw 1610 may move (rotate) relative to the second jaw 1612 to move the jaws 1610, 1612 between open and closed positions. In yet other embodiments, the jaws 1610, 1612 may comprise bifurcating jaws where both jaws 1610, 1612 move simultaneously between open and closed positions.

In the illustrated example, the first jaw 1610 is referred to as a "cartridge" or "channel" jaw, and the second jaw 1612 is referred to as an "anvil" jaw. The first jaw 1610 includes a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In an articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may also include a drive housing or "handle" 1614, and the shaft 1602 extends longitudinally through the handle 1614. The handle 1614 houses an actuation system designed to move the shaft 1602 relative to the handle 1614 in z-axis translation. Other actuation systems housed within the handle 1614 may be designed to facilitate articulation of the wrist 1606 and actuation (operation) of the end effector 1604 (e.g., clamping, firing, rotation, articulation, energy delivery, etc.). In some embodiments, the actuation systems and mechanisms housed within the handle 1614 may be actuatable to move (translate) a plurality of drive members (mostly obscured in FIG. 16) that extend along at least a portion of the shaft 1602, either on the exterior or within the interior of the shaft 1602. Example drive members include, but are not limited to, cables, bands, lines, cords, wires, woven wires, ropes, strings, twisted strings, elongate members, belts, shafts, flexible shafts, drive rods, or any combination thereof. The drive members can be made from a variety of materials including, but not limited to, a metal (e.g., tungsten, stainless steel, nitinol, etc.) a polymer (e.g., ultra-high molecular weight polyethylene), a synthetic fiber (e.g., KEVLAR®, VECTRAN®, etc.), an elastomer, or any combination thereof.

Selective actuation of one or more of the drive members, for example, may cause the shaft 1602 to translate relative to the handle 1614, as indicated by the arrows B (i.e., z-axis translation), and thereby advance or retract the end effector 1602. Selective actuation of one or more other drive members may cause the end effector 1604 to articulate (pivot) relative to the shaft 1602 at the wrist 1606. Selective actuation of one or more additional drive members may cause the end effector 1604 to actuate (operate). Actuating the end effector 1604 depicted in FIG. 16 may entail closing and/or opening the jaws, 1610, 1612 and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot or "guide track" 1616 defined in the first jaw 1610. As it moves distally, the knife transects any tissue grasped between the opposing jaws 1610, 1612, and a plurality of staples contained within the staple cartridge (e.g., housed within the first jaw 1610) are simultaneously urged (cammed) into deforming contact with corresponding anvil surfaces (e.g., pockets) provided on the second jaw 1612. The deployed staples may form multiple rows of staples that seal opposing sides of the transected tissue.

As will be appreciated, however, the end effector 1604 may be replaced with any of the other types of end effectors mentioned herein, and in those cases actuating the end effector 1604 may entail a variety of other actions or movements, without departing from the scope of the disclosure. For example, in some embodiments, the end effector 1604 may be replaced with a vessel sealer and actuating the vessel sealer may further entail triggering energy delivery (e.g., RF energy) to cauterize and/or seal tissue or vessels.

The handle 1614 provides or otherwise includes various coupling features that releasably couple the surgical tool 1600 to an instrument driver 1618 (shown in dashed lines) of a robotic surgical system. The instrument driver 1618 may be similar in some respects to the instrument drivers 1102, 1200 of FIGS. 11 and 12, respectively, and therefore may be best understood with reference thereto. Similar to the instrument drivers 1102, 1200, for example, the instrument driver 1618 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1618.

The handle 1614 includes one or more rotatable drive inputs matable with one or more corresponding drive outputs (not shown) of the instrument driver 1618. Each drive input is actuatable to independently drive (actuate) the actuation systems and mechanisms housed within the handle 1614 and thereby operate the surgical tool 1600. In the illustrated embodiment, the handle 1614 includes a first drive input 1620a, a second drive input 1620b, a third drive input 1620c, a fourth drive input 1620d, a fifth drive input 1620e, and a sixth drive input 1620f. While six drive inputs 1620a-f are depicted, more or less than six may be included in the handle 1614 depending on the application, and without departing from the scope of the disclosure. Each drive input 1620a-f may be matable with a corresponding drive output (not shown) of the instrument driver 1618 such that movement (rotation) of a given drive output correspondingly moves (rotates) the associated drive input 1620a-f and thereby causes various operations of the surgical tool 1600.

In some embodiments, actuation of the first drive input 1620a may cause the knife to fire at the end effector 1604, thus advancing or retracting the knife, depending on the rotational direction of the first drive input 1620a. Actuation of the third drive input 1620c may cause the shaft 1602 to move (translate) relative to the handle 1614 along the longitudinal axis $A_1$, depending on the rotational direction of the third drive input 1620c. In some embodiments, actuation of the second drive input 1620b may shift operation or activation within the handle 1614 between the first and third drive inputs 1620a,c. Consequently, actuation of the second drive input 1620b will dictate whether the knife is fired or whether the shaft 1602 is moved (translated). Actuation of the fourth drive input 1620d may lock and unlock z-axis translation of the shaft 1602, and, as described in more detail herein, actuation of the fifth drive input 1620e may cause articulation of the end effector 1604 at the wrist 1606. Lastly, actuation of the sixth drive input 1620f may cause the jaws 1610, 1612 to open or close, depending on the rotational direction of the sixth drive input 1620f. In some embodiments, as also described in more detail herein, actuation of the sixth drive input 1620f may operate a toggle mechanism 1622 arranged at the proximal end of the shaft 1602, and actuation of the toggle mechanism 1622 may cause the jaws 1610, 1612 to open and close.

Figure 17:
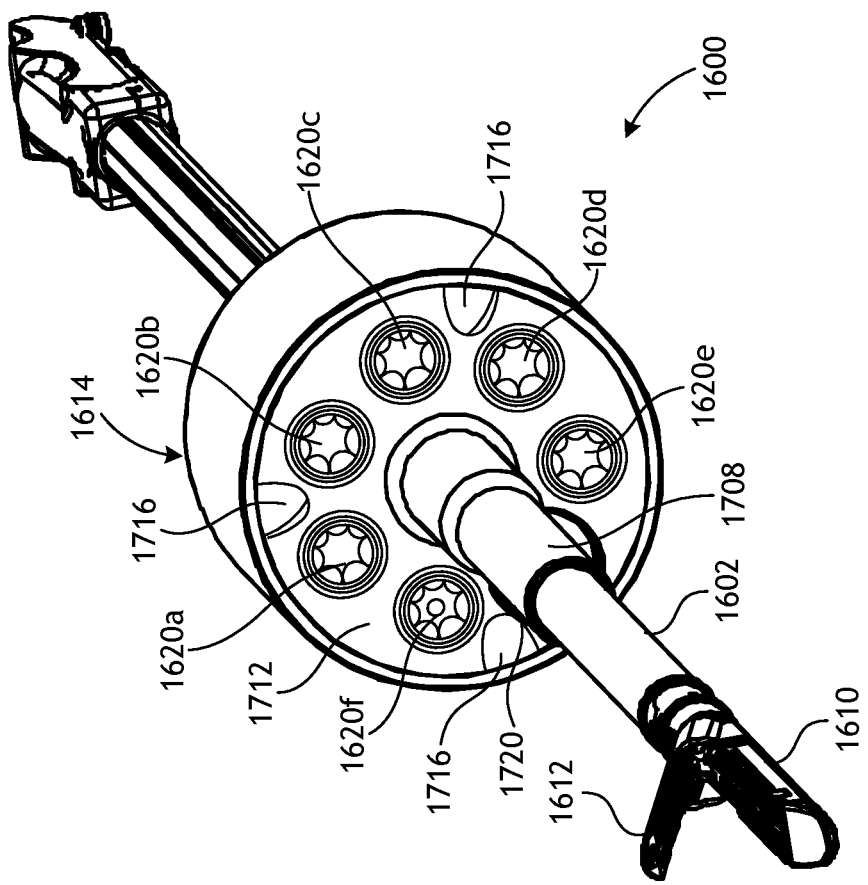
FIG. 17 depicts separated isometric end views of the instrument driver and the surgical tool of FIG. 16.
Figure 17:
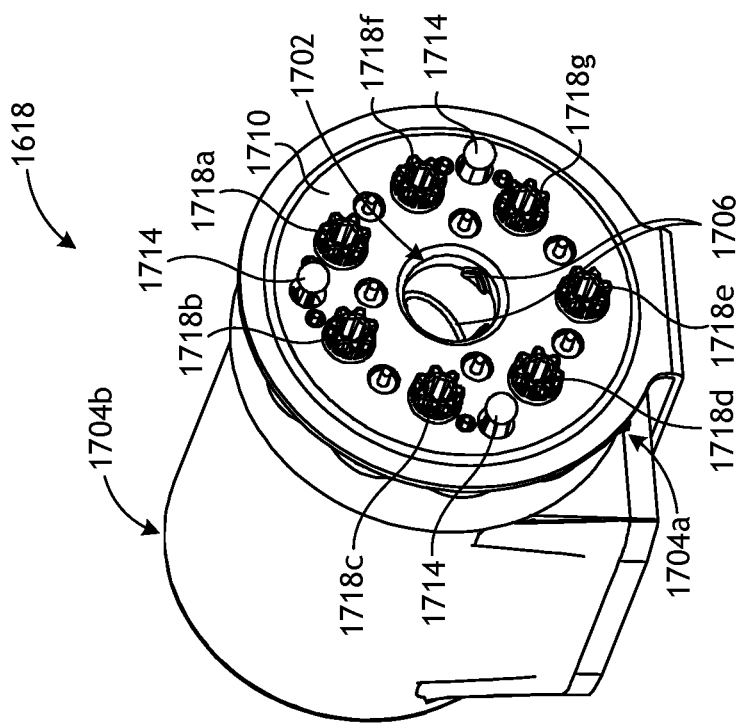

FIG. 17 depicts separated isometric end views of the instrument driver 1618 and the surgical tool 1600 of FIG. 16. With the jaws 1610, 1612 closed, the shaft 1602 and the end effector 1604 can penetrate the instrument driver 1618 by extending through a central aperture 1702 defined longitudinally through the instrument driver 1618 between first and second ends 1704a,b. In some embodiments, to align the surgical tool 1600 with the instrument driver 1618 in a proper angular orientation, one or more alignment guides 1706 may be provided or otherwise defined within the central aperture 1702 and configured to engage one or more corresponding alignment features (not shown) provided on the surgical tool 1600. The alignment feature(s) may comprise, for example, a protrusion or projection (not shown) defined on or otherwise provided by an alignment nozzle 1708 extending distally from the handle 1614. In one or more embodiments, the alignment guide(s) 1706 may comprise a curved or arcuate shoulder or lip configured to receive and guide the alignment feature as the alignment nozzle 1708 enters the central aperture 1702. As a result, the surgical tool 1600 is oriented to a proper angular alignment with the instrument driver 1618 as the alignment nozzle 1708 is advanced distally through the central aperture 1702. In other embodiments, the alignment nozzle 1708 may be omitted and the alignment feature 1712 may alternatively be provided on the shaft 1602, without departing from the scope of the disclosure.

A drive interface 1710 is provided at the first end 1704a of the instrument driver 1618 and is matable with a driven interface 1712 provided on the distal end of the handle 1614. The drive and driven interfaces 1710, 1712 may be configured to mechanically, magnetically, and/or electrically couple the handle 1614 to the instrument driver 1618. To accomplish this, in some embodiments, the drive and driven interfaces 1710, 1712 may provide one or more matable locating features configured to secure the handle 1614 to the instrument driver 1618. In the illustrated embodiment, for example, the drive interface 1710 provides one or more interlocking features 1714 (three shown) configured to locate and mate with one or more complementary-shaped pockets 1716 (two shown, one occluded) provided on the driven interface 1712. In some embodiments, the features 1714 may be configured to align and mate with the pockets 1716 via an interference or snap fit engagement, for example.

The instrument driver 1618 also includes one or more drive outputs that extend through the drive interface 1710 to mate with corresponding drive inputs 1620a-f provided at the distal end of the handle 1614. More specifically, the instrument driver 1618 includes a first drive output 1718a matable with the first drive input 1620a, a second drive output 1718b matable with the second drive input 1620b, a third drive output 1718b matable with the third drive input 1620c, a fourth drive output 1718d matable with the fourth drive input 1620d, a fifth drive output 1718e matable with the fifth drive input 1620e, and a sixth drive output 1718f matable with the sixth drive input 1620f. In some embodiments, as illustrated, the drive outputs 1718a-f may define splines or features designed to mate with corresponding splined receptacles of the drive inputs 1620a-f. Once properly mated, the drive inputs 1620a-f will share axes of rotation with the corresponding drive outputs 1718a-f to allow the transfer of rotational torque from the drive outputs 1718a-f to the corresponding drive inputs 1620a-f. In some embodiments, each drive output 1718a-f may be spring loaded and otherwise biased to spring outwards away from the drive interface 1710. Each drive output 1718a-f may be capable of partially or fully retracting into the drive interface 1710.

In some embodiments, the instrument driver 1618 may include additional drive outputs, depicted in FIG. 17B as a seventh drive output 1718g. The seventh drive output 1718g may be configured to mate with additional drive inputs (not shown) of the handle 1614 to help undertake one or more additional functions of the surgical tool 1600. In the illustrated embodiment, however, the handle 1614 does not include additional drive inputs matable with the seventh drive output 1718g. Instead, the driven interface 1712 defines a corresponding recess 1720 (partially occluded) configured to receive the seventh drive output 1718g. In other applications, however, a seventh drive input (not shown) could be included in the handle 1614 to mate with the seventh drive output 1718g, or the surgical tool 1600 might be replaced with another surgical tool having a seventh drive input, which would be driven by the seventh drive output 1718g.

While not shown, in some embodiments, an instrument sterile adapter (ISA) may be placed at the interface between the instrument driver 1618 and the handle 1614. In such applications, the interlocking features 1714 may operate as alignment features and possible latches for the ISA to be placed, stabilized, and secured. Stability of the ISA may be accomplished by a nose cone feature provided by the ISA and extending into the central aperture 1702 of the instrument driver 1618. Latching can occur either with the interlocking features 1714 or at other locations at the interface. In some cases, the ISA will provide the means to help align and facilitate the latching of the surgical tool 1600 to the ISA and simultaneously to the instrument driver 1618.

Shaft Proximal End Load Reduction Linkage for a Cable Driven Jaw Closure System

Figure 18:
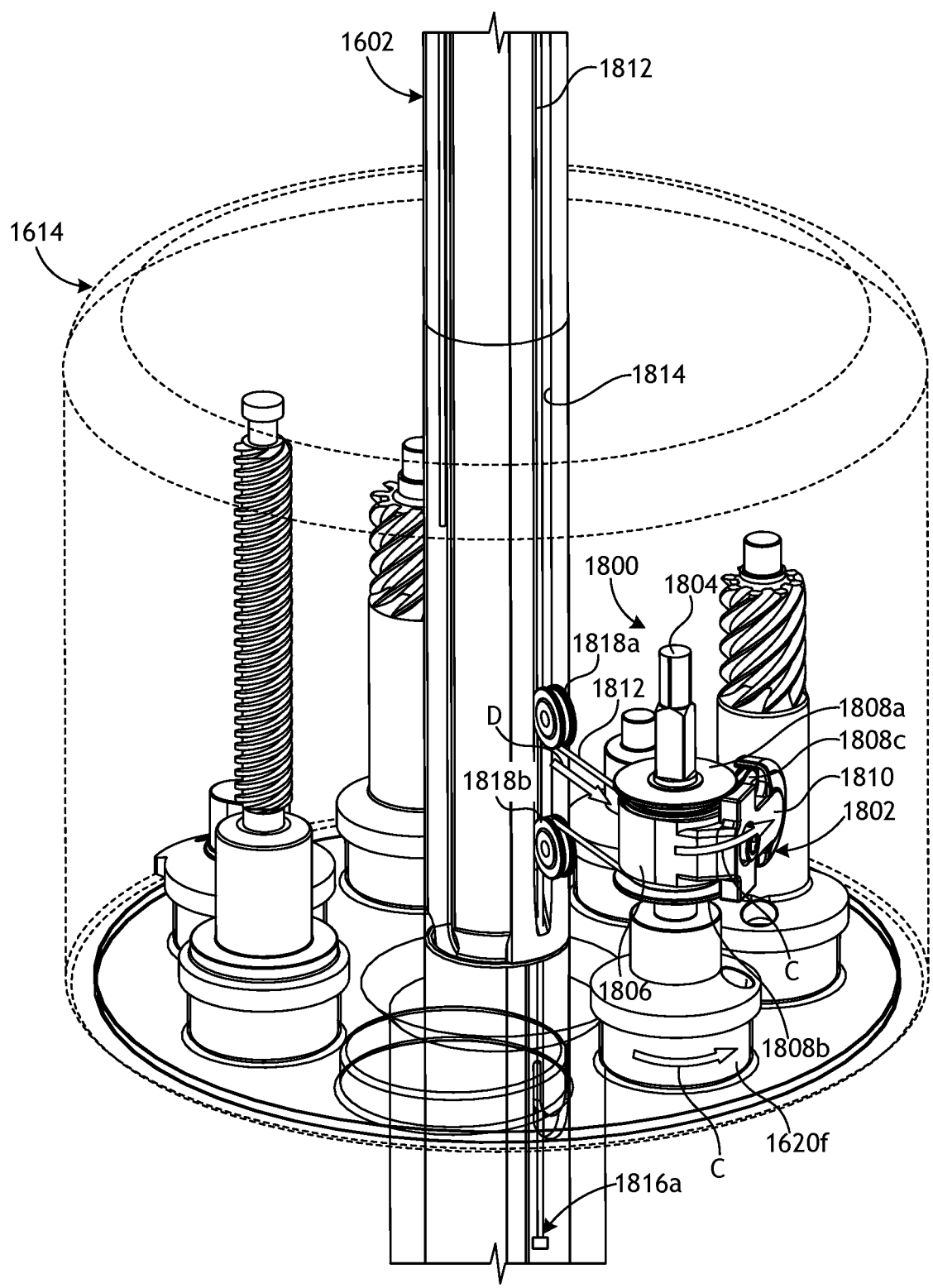
FIG. 18 is an enlarged isometric view of the handle of FIG. 16 depicting an example actuation system, according to one or more embodiments.

FIG. 18 is an enlarged isometric view of the handle 1614 of FIGS. 16-17 and depicting an example actuation system 1800, according to one or more embodiments. The outer body of the handle 1614 is shown in phantom to enable viewing of the internal mechanisms and components housed within the handle 1614, including the actuation system 1800. Various other actuation systems and component parts of the handle 1614 are omitted in FIG. 18 for simplicity.

The actuation system 1800 may alternately be referred to as an "accumulator system" or "cable differential system". According to one or more embodiments, the actuation system 1800 may be operable (actuatable) to open and close the jaws 1610, 1612 (FIGS. 16-17) at the end effector 1604 (FIG. 16). Accordingly, the actuation system 1800 may include or otherwise be operatively coupled to the sixth drive input 1620f, as briefly mentioned above. Depending on the rotational direction of the sixth drive input 1620f, via operation of the sixth drive output 1718f (FIG. 17), the jaws 1610, 1612 may be actuated to open or allowed to close. In other embodiments, however, the actuation system 1800 may be designed to carry out other functions (operations) of the surgical tool 1600 (FIG. 16) or the end effector 1604, such as causing the shaft 1602 to translate relative to the handle 1614, causing the end effector 1604 to articulate, or causing the end effector 1604 to "fire," without departing from the scope of this disclosure.

As illustrated, the actuation system 1800 includes an accumulator 1802 coupled to a drive shaft 1804 extending from the sixth drive input 1620f The drive shaft 1804 may be coupled to or form part of the sixth drive input 1620f such that rotation of the sixth drive input 1620f correspondingly rotates the drive shaft 1804 and simultaneously rotates the accumulator 1802 in the same angular direction.

The accumulator 1802 may include a body 1806 coupled to or forming part of the drive shaft 1804, and the body 1806 may interpose a first or "upper" accumulator pulley 1808a and a second or "lower" accumulator pulley 1808b. The upper and lower accumulator pulleys 1808a,b may be rotatably mounted to the drive shaft 1804 and axially offset from each other, thus sharing the same axis of rotation. The accumulator 1802 may further include a third or "side" accumulator pulley 1808c laterally offset from the upper and lower accumulator pulleys 1808a,b. The side accumulator pulley 1808c, for example, may be rotatably mounted to a lateral arm 1810 extending from the body 1806.

The actuation system 1800 may further include a drive member 1812 that extends longitudinally along at least a portion of the shaft 1602. In the illustrated embodiment, the drive member 1812 comprises a cable or wire and, therefore, will be referred to herein as "the drive cable 1812". In other embodiments, however, the drive cable 1812 may comprise any of the other types of drive members mentioned herein.

As illustrated, the drive cable 1812 may be received and extend within a groove 1814 defined in the shaft 1602. In other embodiments, however, the drive cable 1812 may alternatively be received within the interior of the shaft 1602 or extend along an exterior surface of the shaft 1602, without departing from the scope of the disclosure.

Figure 19:
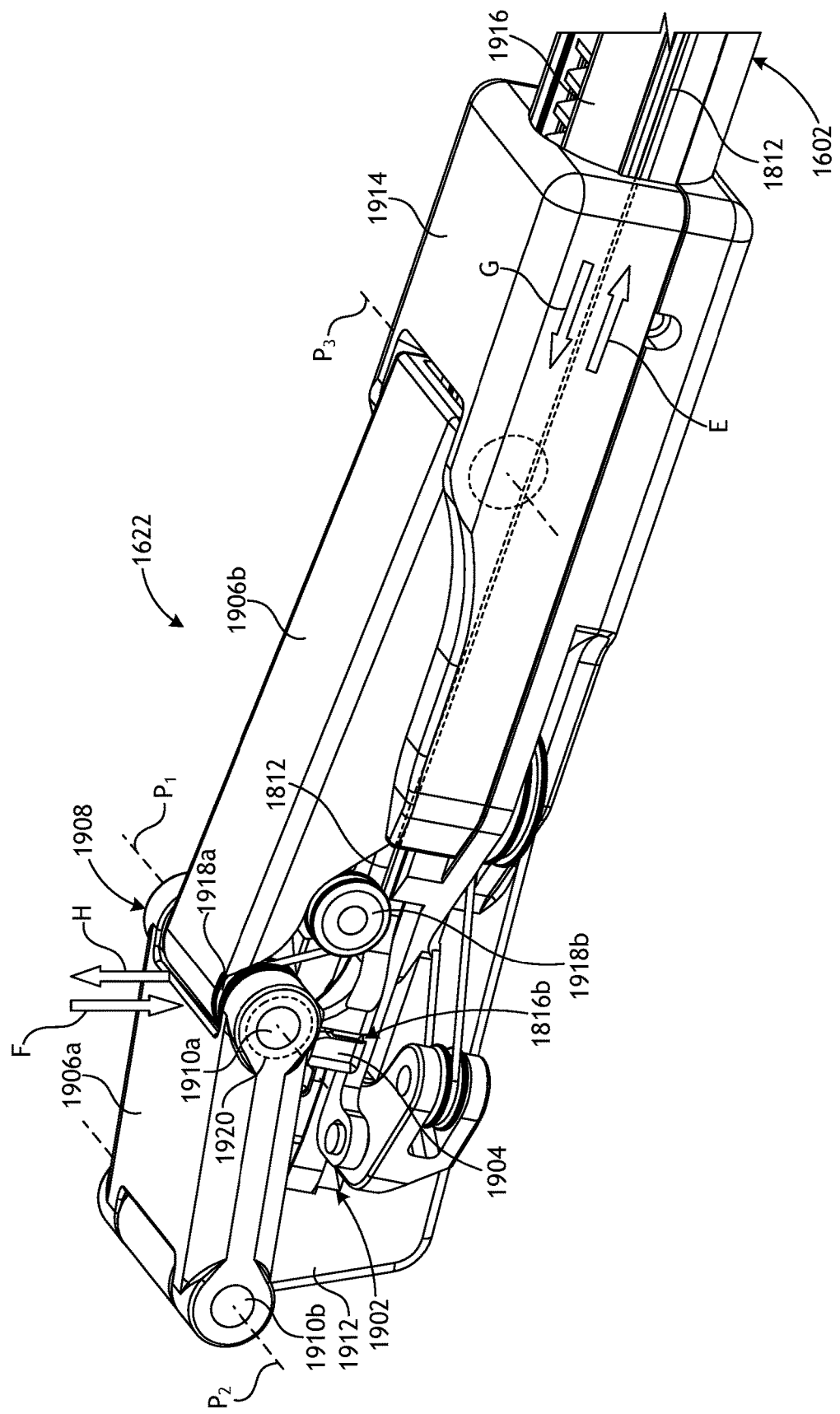
FIG. 19 is an isometric side view of the toggle mechanism of FIG. 16, according to one or more embodiments of the present disclosure.

A first or "distal" end 1816a of the drive cable 1812 may be anchored to the shaft 1602 below (distal to) the handle 1614, and a second or "proximal" end 1816b (see FIG. 19) of the drive cable 1812 may be anchored to the shaft 1602 above (proximal to) the handle 1614. In some embodiments, the proximal end 1816b of the drive cable 1812 may be anchored at or near a proximal end of the shaft 1602 and adjacent the toggle mechanism 1622 (FIGS. 16 and 19). As discussed in more detail below, actuation of the accumulator 1802 may cause the drive cable 1812 to act on the toggle mechanism 1622, which may be designed to open and close the jaws 1610, 1612 (FIGS. 16-17).

As illustrated, the drive cable 1812 may also extend or be threaded (guided) through the accumulator 1802 within the body of the handle 1614. The actuation system 1800 may further include a first or "upper" idler pulley 1818a and a second or "lower" idler pulley 1818b. The upper and lower idler pulleys 1818a,b may each be rotatably coupled to the handle 1614. The upper idler pulley 1818a may be arranged and otherwise configured to redirect the drive cable 1812 between the shaft 1602 and the upper accumulator pulley 1808a, and the lower idler pulley 1818b may be arranged and otherwise configured to redirect the drive cable 1812 between the shaft 1602 and the lower accumulator pulley 1808b.

The side accumulator pulley 1808c may be arranged to receive and redirect the drive cable 1812 between the upper and lower accumulator pulleys 1808a,b. More specifically, in some embodiments, the upper and lower accumulator pulleys 1808a,b may be arranged for rotation in respective parallel planes, while the side accumulator pulley 1808c may be arranged for rotation in a plane that is 90° offset from the parallel planes in order to redirect the drive cable 1812 between the upper and lower accumulator pulleys 1808a,b. In one embodiment, for example, the parallel planes of the upper and lower accumulator pulleys 1808a,b may be characterized as extending substantially horizontal, and the plane of the side accumulator pulley 1808c may be characterized as extending substantially vertical and otherwise 90° offset from the horizontal planes. In other embodiments, however, the planes of the upper and lower accumulator pulleys 1808a,b and the side accumulator pulley 1808c need not be 90° offset from each other. Moreover, the upper and lower accumulator pulleys 1808a,b need not be arranged for rotation in respective parallel planes, but may alternatively be arranged in non-parallel planes, without departing from the scope of the disclosure.

As mentioned above, the actuation system 1800 may be actuated or operated by rotating the sixth drive input 1620f, via operation of the sixth drive output 1718f (FIG. 17). Rotating the sixth drive input 1620f in a first angular direction C will correspondingly rotate the drive shaft 1804 and the accumulator 1802 in the same direction C and about the same rotational axis. Because the distal end 1816a of the drive cable 1812 is anchored to the shaft 1602 distal to the handle 1614, the drive cable 1812 may be drawn (pulled) into the accumulator 1802 at the upper accumulator pulley 1808a as the accumulator 1802 rotates in the direction C. This is shown by the arrow D. Upon releasing the torque at the sixth drive input 1620f, or otherwise reversing the direction of the sixth drive output 1718f, the drive shaft 1804 and the accumulator 1802 will rotate opposite the direction C, and a length of the drive cable 1812 may correspondingly be paid out (fed) to the shaft 1602 from the upper accumulator pulley 1808a in a direction opposite the arrow D. As discussed in more detail below, drawing or paying out the drive cable 1812 into or from the accumulator 1802 correspondingly acts on the toggle mechanism 1622 (FIGS. 16 and 19) at the proximal end of the shaft 1602, and operation of the toggle mechanism 1622 may result in the jaws 1610, 1612 (FIGS. 16-17) closing or opening, depending on the direction of the drive cable 1812.

In some embodiments, the actuation system 1800 may be decoupled from shaft 1602 insertion. More specifically, the accumulator pulleys 1808a-c and the idler pulleys 1818a,b are able to freely rotate (e.g., "free wheel") and are otherwise not driven during operation of the handle 1614. Consequently, as the shaft 1602 moves longitudinally relative to the handle 1614 in z-axis translation, the drive cable 1812 is able to freely run (course) through the accumulator 1802 between the upper and lower idler pulleys 1818a,b. Moreover, since the accumulator pulleys 1808a-c and the idler pulleys 1818a,b are able to freely rotate, the actuation system 1800 can be operated simultaneously during shaft 1602 translation.

FIG. 19 is an enlarged, isometric side view of the toggle mechanism 1622 of FIG. 16, according to one or more embodiments of the present disclosure. As illustrated, the toggle mechanism 1622 may be arranged at or near a proximal end 1902 of the shaft 1602. The drive cable 1812 extends from the handle 1614 (FIG. 18) to the toggle mechanism 1622, and the proximal end 1816b of the drive cable 1812 may be secured (anchored) to the shaft 1602 at or near the proximal end 1902. In at least one embodiment, the drive cable 1812 may be secured to the shaft 1602 at a cable anchoring location 1904 coupled to or forming part of the shaft 1602.

In some embodiments, the toggle mechanism 1622 may comprise a two-bar linkage system. More specifically, the toggle mechanism 1622 may include a first or "proximal" link 1906a and a second or "distal" link 1906b rotatably coupled to the proximal link 1906a at a hinge joint 1908. The hinge joint 1908 may include a first axle 1910a that couples the proximal and distal links 1906a,b, and the first axle 1910a may extend along a first pivot axis $P_1$. During operation of the toggle mechanism 1622, the proximal and distal links 1906a,b may be configured to pivot about the first pivot axis $P_1$.

The proximal link 1906a may also be rotatably coupled to the shaft 1602 and, more particularity, to a tail piece 1912 secured to the shaft 1602 at or near the proximal end 1902. The proximal link 1906a may be rotatably coupled to the tail piece 1912 at a second axle 1910b through which a second pivot axis $P_2$ extends. Moreover, the distal link 1906b may also be rotatably coupled to a pusher member 1914 and pivotable about a third pivot axis $P_3$ extending through the distal link 1906b and the pusher member 1914. In some embodiments, the first, second, and third pivot axes $P_{1-3}$ may be substantially parallel to each other.

Figure 20:
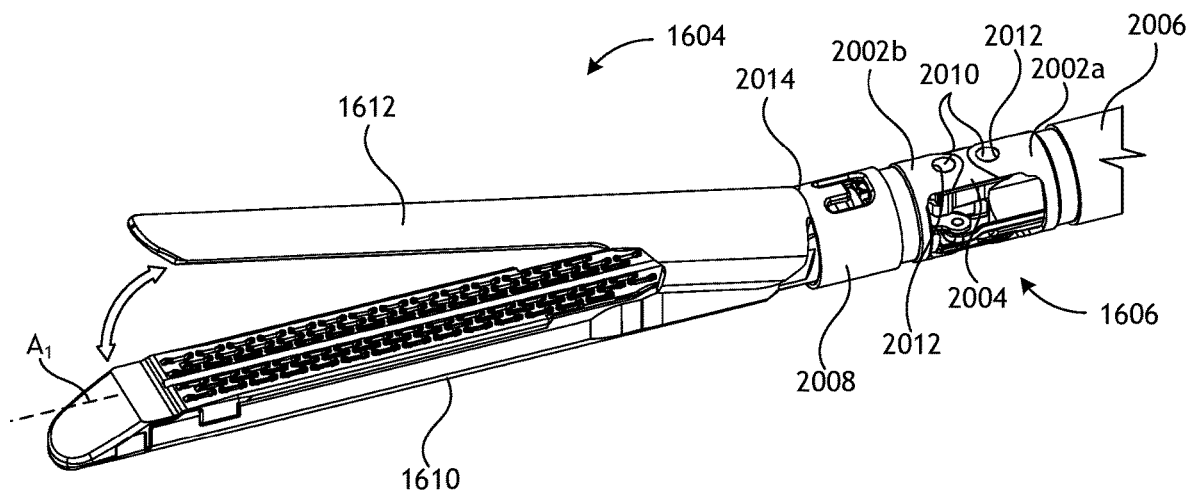
FIG. 20 is an enlarged isometric view of the end effector and the wrist of FIG. 16, according to one or more embodiments.

The pusher member 1914 may be mounted to the shaft 1602 and, more particularly, to a movable shaft portion 1916 that forms part of the shaft 1602. The pusher member 1914 may be engageable with the movable shaft portion 1916 such that longitudinal movement of the pusher member 1914 resulting from movement of the distal link 1906b may correspondingly move the movable shaft portion 1916 in the same axial direction. While forming part of the shaft 1602, the movable shaft portion 1916 may be able to translate longitudinally relative to remaining portions of the shaft 1602 as acted upon by the pusher member 1914. The movable shaft portion 1916 extends distally and is operatively coupled (either directly or indirectly) to a closure tube 2006 (see FIG. 20), which may comprise an outer portion of the shaft 1602 that extends to the end effector 1604 (FIGS. 16 and 20).

The toggle mechanism 1622 may further include various pulleys configured to receive and redirect the drive cable 1812. In the illustrated embodiment, for example, the toggle mechanism 1622 includes first and second linkage pulleys 1918a and 1918b. The first linkage pulley 1918a may be rotatably mounted to the first axle 1910a at the hinge joint 1908. The first linkage pulley 1918a receives the drive cable 1812 from the second linkage pulley 1918b and feeds the drive cable 1812 to the cable anchoring location 1904. The second linkage pulley 1918b may be secured to the shaft 1602 at or near the proximal end 1902. In at least one embodiment, however, the second linkage pulley 1918b may be omitted from the toggle mechanism 1622 and the drive cable 1812 may be fed directly to the first linkage pulley 1918a, without departing from the scope of the disclosure.

The toggle mechanism 1622 may be movable (pivotable) between a first or "actuated" position, where the hinge joint 1908 is moved (pivoted) toward the shaft 1602, and a second or "extended" position, where the hinge joint 1908 is moved (pivoted) away from the shaft 1602. The hinge joint 1908 is depicted in FIG. 19 at a point between the actuated and extended positions. Moving (pivoting) the toggle mechanism 1622 to the actuated position will cause the jaws 1610, 1612 (FIGS. 16-17) at the end effector 1604 (FIG. 16) to close, and moving (pivoting) the toggle mechanism 1622 to the extended position will cause (or allow) the jaws 1610, 1612 to open.

In some embodiments, the toggle mechanism 1622 may be moved (transitioned) to the actuated position through actuation and operation of the actuation system 1800 of FIG. 18. More specifically, as the actuation system 1800 is actuated, as generally described above, the drive cable 1812 may be drawn by the rotating accumulator 1802 (FIG. 18) and correspondingly pulled distally along the shaft 1602, as shown by the arrow E. As the drive cable 1812 is pulled distally E, and since it is anchored to the shaft 1602 at the cable anchoring location 1904, the drive cable 1812 will act on the hinge joint 1908 at the first linkage pulley 1918a and correspondingly urge (pull) the hinge joint 1908 toward the shaft 1602 and the actuated position, as shown by the arrow F. As the hinge joint 1908 moves toward the actuated position, the distal link 1906b may correspondingly drive (move) the pusher member 1914 distally E, which correspondingly moves the movable shaft portion 1916 in the same direction. Moving the movable shaft portion 1916 distally E may act on the closure tube 2006 (FIG. 20) to close the jaws 1610, 1612 (FIGS. 16 and 20) at the end effector 1604 (FIGS. 16 and 20).

As will be appreciated, the toggle mechanism 1622 may provide a mechanical advantage. More specifically, because work=force×distance, as the proximal and distal links 1906a,b approach 0° relative to each other (e.g., straight), the distance that affects translation of the shaft portion 1916 is smaller, thus allowing more force. Consequently, the force/torque required by the drive input 1620f (FIG. 18) to cause actuation of the toggle mechanism 1622 is decreased to effectuate the end effector jaw closure. For example, the force to close the jaws 1610, 1612 (FIGS. 16 and 20) may need 200 lbs of pull force, and the input torque to operate the toggle mechanism 1622 to generate that 200 lbs of pull is less due to the mechanical advantage of the toggle mechanism 1622. The load on the drive input 1620f can be more or less depending on the moment arms (e.g., layout of the hinge joint 1908) of the toggle mechanism 1622. Accordingly, mechanical advantage increases with stroke during operation. In other words, the relationship between force and distance may be intentionally varied throughout the stroke; e.g., small input=large distance output at the beginning of the stroke, and large input=small distance output at the end of the stroke. This amplifies mechanical advantage and load application when the jaws 1610, 1612 (FIGS. 16 and 20) are nearing close and compressing against the resistance of tissue grasped between the jaws 1610, 1612.

Upon disengaging (ceasing) operation of the actuation system 1800 (FIG. 18), or otherwise reversing operation of the actuation system 1800, tension in the drive cable 1812 in the distal direction E may be released. The drive cable 1812 may then be able to be paid out of the accumulator 1802 (FIG. 18) to the shaft 1602 and allowed to be drawn (moved) proximally along the shaft 1602, as shown by the arrow G. In some embodiments, the toggle mechanism 1622 may be naturally biased toward the extended position and, therefore, continuously urged away from the shaft 1602, as shown by the arrow H. In such embodiments, for example, the hinge joint 1908 may be spring loaded or otherwise include one or more torsion springs 1920 (one shown in dashed lines) that act on the hinge joint 1908 to urge the links 1906a,b to pivot away from the shaft 1602 to the natural positon. As the hinge joint 1908 moves in the direction H toward the extended position, the drive cable 1812 is correspondingly drawn (pulled) proximally G. Moreover, as the hinge joint 1908 moves to the extended position, the distal link 1906b may correspondingly pull (move) the pusher member 1914 proximally G, which correspondingly moves the movable shaft portion 1916 in the same direction. Moving the movable shaft portion 1916 proximally G may act on the closure tube 2006 (FIG. 20) and allow the jaws 1610, 1612 (FIGS. 16 and 20) at the end effector 1604 (FIGS. 16 and 20) to open.

Referring now to FIG. 20, with continued reference to FIGS. 18-19, depicted is an enlarged isometric view of the end effector 1604 and the wrist 1606, according to one or more embodiments. As illustrated, the wrist 1606 may include a first or "proximal" clevis 2002a, a second or "distal" clevis 2002b, and a closure link 2004 configured to operatively couple the proximal and distal devises 2002a,b across the wrist 1606. The proximal clevis 2002a may be coupled to or otherwise form part of the distal end of a closure tube 2006, which, as discussed above, may form an outer portion of the shaft 1602 (FIGS. 16-19) and may be operatively coupled (either directly or indirectly) to the movable shaft portion 1916 (FIG. 19). The distal clevis 2002b may be coupled to or otherwise form part of a closure ring 2008 arranged adjacent the jaws 1610, 1612.

Axial movement of the closure tube 2006 along the longitudinal axis $A_1$, as acted upon by the movable shaft portion 1916 (FIG. 19) as generally described above, correspondingly moves the proximal clevis 2002a in the same axial direction. The closure link 2004 may be configured to transmit the axial load through (across) the wrist 1606 to close the jaws 1610, 1612 of the end effector 1604. More specifically, the closure link 2004 defines a pair of pins 2010 configured to mate with corresponding apertures 2012 defined in each of the proximal and distal devises 2002a,b. The closure link 2004 may transmit the closure load or translation movement of the closure tube 2006 from the distal clevis 2002b to the proximal clevis 2002a and the closure ring 2008 will correspondingly push or pull on the upper jaw 1612 to close or open the upper jaw 1612. To close the upper jaw 1612, the closure ring 2008 is forced distally against a shoulder 2014 at or near the back of the upper jaw 1612, which urges the upper jaw 1612 to pivot down and to the closed position. To open the upper jaw 1612, the closure ring 2008 is retracted proximally away from the shoulder 2014 by retracting the closure tube 2006.

In some embodiments, proximal movement of the closure ring 2008 helps pull the upper jaw 1612 back toward the open position. In other embodiments, however, the upper jaw 1612 may be spring loaded and biased to the open position. In such embodiments, the spring force of the upper jaw 1612 may be sufficient to retract the closure ring 2008 and the closure tube 2006. Moreover, in such embodiments, the spring force of the upper jaw 1612 may be sufficient to move (transition) the toggle mechanism 1622 (FIG. 19) toward the extended position through interconnection of the closure tube 2006, the movable shaft portion 1916 (FIG. 19), the pusher member 1914 (FIG. 19), and the distal link 1906b (FIG. 19). Alternatively, both the hinge joint 1908 (FIG. 19) and the upper jaw 1612 may be spring loaded to cooperatively urge the toggle mechanism 1622 toward the extended position.

Robotic Instrument with Proximal End Articulation System

Figure 21:
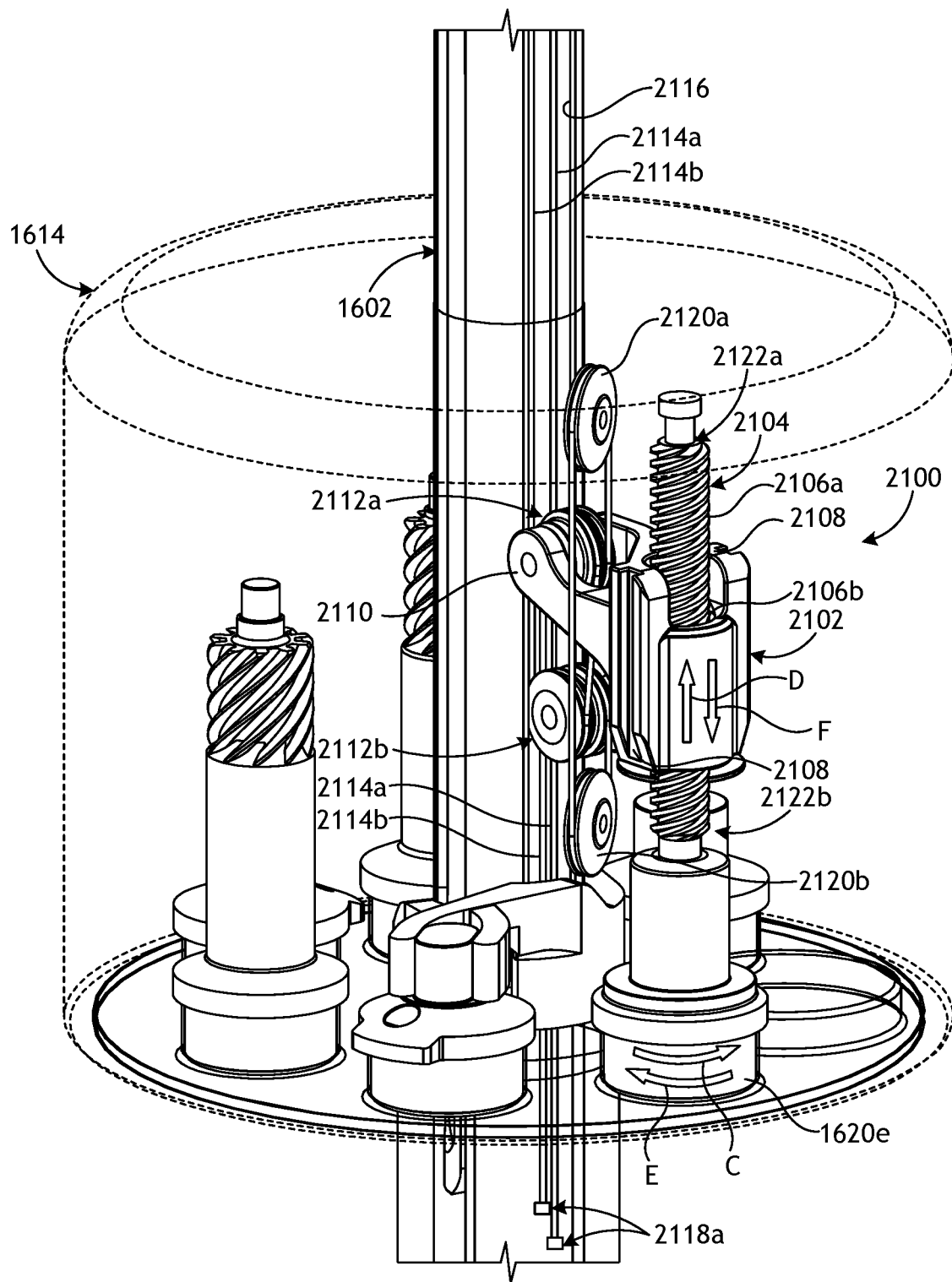
FIG. 21 is an enlarged isometric view of the handle of FIGS. 16-17 depicting another example actuation system, according to one or more embodiments.

FIG. 21 is an enlarged isometric view of the handle 1614 of FIGS. 16-17 depicting another example actuation system 2100, according to one or more embodiments. The outer body of the handle 1614 is again shown in phantom to enable viewing of the internal mechanisms housed within the handle 1614, including the actuation system 2100. Various other actuation systems and component parts of the handle 1614 are omitted in FIG. 21 for simplicity.

According to one or more embodiments, the actuation system 2100 may be operable (actuatable) to cause the end effector 1604 (FIG. 16) to articulate at the wrist 1606 (FIGS. 16-17). Accordingly, the actuation system 2100 may include or otherwise be operatively coupled to the fifth drive input 1620e, as briefly mentioned above. Rotation (actuation) of the fifth drive input 1620e, via operation of the fifth drive output 1718e (FIG. 17), may cause the actuation system 2100 to operate, which results in articulation of the end effector 1604. In other embodiments, however, the actuation system 2100 may be designed to carry out other functions (operations) of the surgical tool 1600 (FIG. 16) or the end effector 1604, such as causing the shaft 1602 to translate relative to the handle 1614, opening or closing the jaws 1610, 1612 (FIGS. 16-17) at the end effector 1604, or causing the end effector 1604 to "fire," without departing from the scope of this disclosure.

As illustrated, the actuation system 2100 includes a nut 2102 coupled to a lead screw 2104 extending from the fifth drive input 1620e. The lead screw 2104 may be coupled to or form part of the fifth drive input 1620e such that rotation of the fifth drive input 1620e correspondingly rotates the lead screw 2104 in the same direction. Moreover, the lead screw 2104 defines external helical threading 2106a matable with internal helical threading 2106b defined by the nut 2102. Consequently, as the lead screw 2104 rotates, threaded engagement between the external and internal threading 2106a,b urges the nut 2102 to traverse the lead screw 2104 either proximally or distally, depending on the rotation direction of the lead screw 2104. In some embodiments, the internal threading 2106b may be defined on the nut 2102, but in other embodiments, the internal threading 2106b may be defined on a linear slide element (not shown) disposed within and coupled to the nut 2102.

In some embodiments, the nut 2102 may provide or otherwise define one or more channel guides 2108 (two shown). The channel guides 2108 may be configured to receive opposing guide structures (not shown) provided by the handle 1614. As the nut 2102 traverses the lead screw 2104, the guide structures correspondingly traverse the channel guides 2108 and help prevent the nut 2102 from rotating as the lead screw 2104 rotates.

The nut 2102 may provide or otherwise include an armature 2110 extending laterally from the nut 2102 and toward the shaft 1602. In some embodiments, a first or "upper" pulley 2112a may be rotatably mounted to the armature 2110, such as at or near the end of the armature 2110. A second or "lower" pulley 2112b may be rotatably coupled to the handle 1614 and axially offset from the upper pulley 2112a. Accordingly, movement of the nut 2102 along the lead screw 2104 will correspondingly move the upper pulley 2112a toward or away from the lower pulley 2112b, which remains stationary relative to the handle 1614 during operation. The pulleys 2112a,b may comprise double barrel pulleys (alternately referred to as "double pulleys") capable of accommodating two drive members or drive cables.

The actuation system 2100 may further include a first drive member 2114a and a second drive member 2114b that extend longitudinally along at least a portion of the shaft 1602 and interact with the pulleys 2112a,b. In the illustrated embodiment, each drive member 2114a,b comprises a cable or wire and, therefore, will be referred to herein as "drive cables 2114a,b". In other embodiments, however, the drive cables 2114a,b may comprise any of the other types of drive members mentioned herein. As illustrated, the drive cables 2114a,b may be received and extend within a groove 2116 defined in the shaft 1602. In other embodiments, however, the drive cables 2114a,b may alternatively be received within the interior of the shaft 1602 or extend along an exterior surface of the shaft 1602, without departing from the scope of the disclosure.

A first or "distal" end 2118a of each drive cable 2114 may be anchored to the shaft 1602 below (distal to) the handle 1614, and a second or "proximal" end 2118b (see FIGS. 22A-22B) of each drive cable 2114 may be anchored to the shaft 1602 above (proximal to) the handle 1614. As discussed in more detail below, the proximal end 2118b of each drive cable 2114 may be anchored at or near the proximal end 1902 (FIGS. 22A-22B) of the shaft 1602. Accordingly, the drive cables 2114a,b may be anchored both proximally and distally along the shaft 1602.

The actuation system 2100 may further include a first or "upper" idler pulley 2120a and a second or "lower" idler pulley 2120b. The upper and lower idler pulleys 2120a,b may each be rotatably coupled to the handle 1614 and longitudinally (axially, vertically, etc.) offset from each other. More specifically, in some embodiments, the upper idler pulley 2120a may be mounted within the handle 1614 at or above a proximal end 2122a of the external threading 2106a, and the lower idler pulley 2120b may be mounted within the handle 1614 at or below a distal end 2122b of the external threading 2106a. Consequently, movement of the nut 2102 along the lead screw 2104 may not be able to surpass the position of the idler pulleys 2120a,b on either end 2122a,b of the lead screw 2104.

In some embodiments, the pulleys 2112a,b may have parallel axes of rotation. In some embodiments, the idler pulleys 2120a,b may also have parallel axes of rotation, but may alternatively have non-parallel axes of rotation. In some embodiments, the pulleys 2112a,b may be arranged for rotation in the same plane, while the idler pulleys 2120a,b may be arranged for rotation in a plane that is offset from the rotation plane of the pulleys 2112a,b. In at least one embodiment, the idler pulleys 2120a,b may be arranged for rotation in non-parallel planes, but nonetheless offset from the rotation plane of the pulleys 2112a,b, without departing from the scope of the disclosure.

As illustrated, the drive cables 2114a,b may be configured to extend or be threaded (guided) through the actuation system 2100 and, more particularly, through the pulleys 2112a,b and the idler pulleys 2120a,b within the body of the handle 1614. The upper pulley 2112a may be arranged and otherwise configured to receive the first drive cable 2114a from a proximal portion of the shaft 1602 and redirect the first drive cable 2114a from the shaft 1602 to the upper idler pulley 2120a. The upper idler pulley 2120a may then redirect the first drive cable 2114a to the lower idler pulley 2120b, which may be arranged to redirect the first drive cable 2114a to the lower pulley 2112b. The lower pulley 2112b may be arranged to redirect the first drive cable 2114a back to the shaft 1602 (e.g., within the groove 2116) to extend distally. In contrast, the lower pulley 2112b may be arranged and otherwise configured to receive the second drive cable 2114b from the proximal portion of the shaft 1602 and redirect the second drive cable 2114b from the shaft 1602 to the upper pulley 2112a. The upper pulley 2112a may then be configured to redirect the second drive cable 2114a back to the shaft 1602 (e.g., within the groove 2116) to extend distally therefrom.

As mentioned above, the actuation system 2100 may be actuated or operated by rotating the fifth drive input 1620e, via operation of the fifth drive output 1718e (FIG. 17). Rotating the fifth drive input 1620e in a first angular direction C (e.g., clockwise) will correspondingly rotate the lead screw 2104 in the same direction C and thereby cause the nut 2102 to move proximally along the lead screw 2104, as indicated by the arrow D. Moving the nut 2102 proximally D simultaneously moves the upper pulley 2112a away from the lower pulley 2112b. In contrast, rotating the fifth drive input 1620e in a second angular direction E (e.g., counter-clockwise) opposite the first angular direction C will correspondingly rotate the lead screw 2104 in the same direction E and thereby cause the nut 2102 to move distally along the lead screw 2104, as indicated by the arrow F. Moving the nut 2102 distally F simultaneously moves the upper pulley 2112a toward the lower pulley 2112b.

Actuation or operation of the actuation system 2100 may result in antagonistic manipulation of the drive cables 2114a,b that results in articulation of the end effector 1604 (FIG. 16) at the wrist 1606 (FIGS. 16-17). More specifically, movement of the nut 2102 along the lead screw 2104 may result in the overall lengths of the drive cables 2114a,b changing equally and opposite by a factor of two times (2×) the motion of the nut 2102. This is possible since the drive cables 2114a,b are each fixed at opposite ends to the shaft 1602 and guided through (nested within) the upper and lower pulleys 2112a,b, where the upper pulley 2112a is able to move toward or away from the lower pulley 2112b based on rotational direction of the lead screw 2104.

In example operation, as the nut 2102 is actuated to move proximally D along the lead screw 2104 by one (1) unit of length, the actuation system 2100 will pay out (dispense) two (2) units of length of the first drive cable 2114a to the shaft 1602 and simultaneously pay in (draw in) two (2) units of length of the second drive cable 2114b from the shaft 1602. In contrast, as the nut 2102 is actuated to move distally F along the lead screw 2104 by one (1) unit of length, the actuation system 2100 will pay in (draw in) two (2) units of length of the first drive cable 2114a from the shaft 1602 and simultaneously pay out (dispense) two (2) units of length of the second drive cable 2114b to the shaft 1602. Such antagonistic and simultaneous operation of the drive cables 2114a,b helps to articulate the end effector 1604 (FIG. 16) at the wrist 1606 (FIGS. 16-17), as discussed below.

In some embodiments, the actuation system 2100 may be decoupled from shaft 1602 insertion. More specifically, the pulleys 2112a-c and the idler pulleys 2120a,b may be able to freely rotate (e.g., "free wheel") and are otherwise not driven during operation of the handle 1614. Consequently, as the shaft 1602 moves longitudinally relative to the handle 1614 in z-axis translation, the drive cables 2114a,b are able to freely run (course) through the actuation system 2100 and about the pulleys 2112a-c and the idler pulleys 2120a,b. Moreover, since the pulleys 2112a-c and the idler pulleys 2120a,b are able to freely rotate, the actuation system 2100 can be operated simultaneously during shaft 1602 z-axis translation.

Figure 22A:
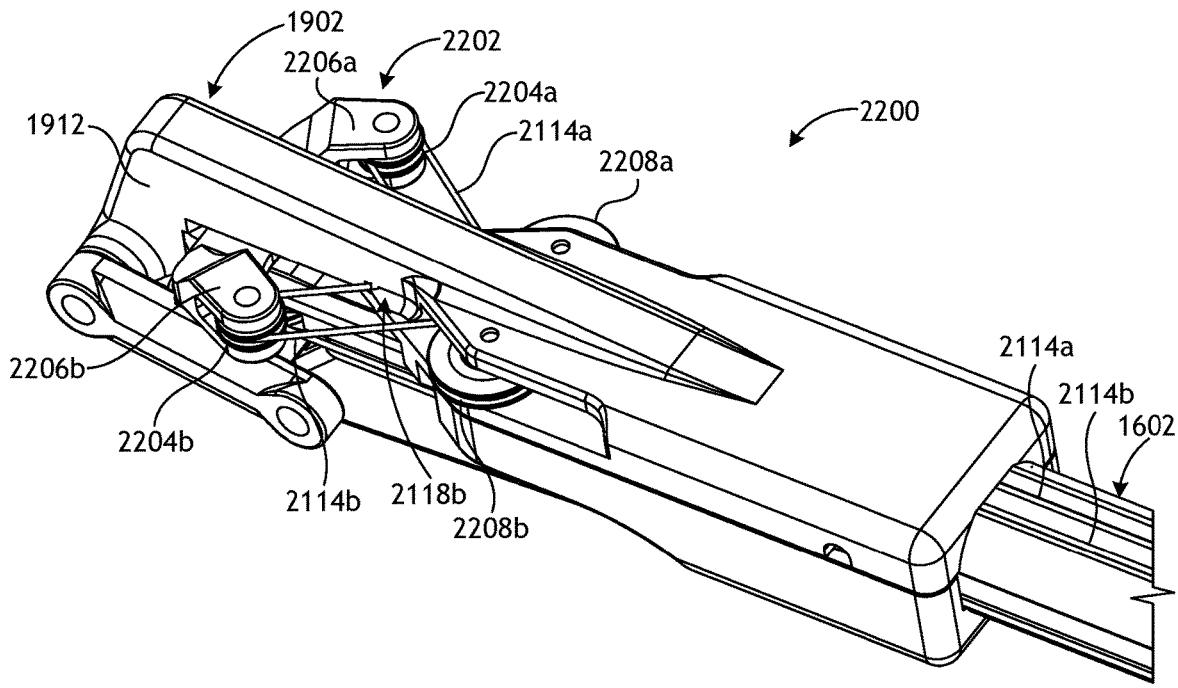
FIG. 22A is an enlarged, isometric side view of an example rocker bar system, according to one or more embodiments of the present disclosure.

FIG. 22A is an enlarged, isometric side view of an example rocker bar system 2200, according to one or more embodiments of the present disclosure. The rocker bar system 2200 may work in conjunction with the actuation system 2100 (FIG. 21) to articulate the end effector 1604 (FIG. 16) at the wrist 1606 (FIGS. 16-17). More specifically, operation of the actuation system 2100 causes the rocker bar system 2200 to actuate and thereby articulate the end effector 1604, as will be discussed below.

The rocker bar system 2200 may be arranged at or near the proximal end 1902 of the shaft 1602. In the illustrated embodiment, for example, the rocker bar system 2200 may be mounted to the tail piece 1912, which is coupled to the proximal end 1902 of the shaft 1602. In at least one embodiment, however, the tail piece 1912 may form part of the rocker bar system 2200.

The drive cables 2114a,b extend from the handle 1614 (FIG. 21) to the rocker bar system 2200, and the proximal ends 2118b of the drive cables 2114a,b may be secured (anchored) to the shaft 1602 at or near its proximal end 1902. In at least one embodiment, for example, the proximal ends 2118b of the drive cables 2114a,b may be secured to the tail piece 1912. The rocker bar system 2200 may further include a rocker bar 2202 pivotably mounted to the shaft 1602 and/or the tail piece 1912, and the rocker bar 2202 may be configured to receive and redirect the drive cables 2114a,b at the proximal end 1902 of the shaft 1602.

The rocker bar system 2200 may further include various pulleys used to receive and redirect the drive cables 2114a,b. In the illustrated embodiment, for example, a first rocker pulley 2204a may be rotatably mounted to a first lateral arm 2206a of the rocker bar 2202, and a second rocker pulley 2204b may be rotatably mounted to a second lateral arm 2206b of the rocker bar 2202. In at least one embodiment, as illustrated, the lateral arms 2206a,b may extend laterally outward past opposing sides of the shaft 1602. As will be appreciated, a mechanical advantage can be gained with the lateral arms 2206a,b extending outward from the pivot point of the rocker bar 2202. The further out the lateral arms 2206a,b extend, the greater the mechanical advantage achieved. Additional mechanical advantage is also obtained by double-wrapping the drive cables 2114a,b around the rocker pulleys 2204a,b. More specifically, if the drive cables 2114a,b terminated at the end of the rocker bar 2202, then there would be no amplification. Routing the drive cables 2114a,b around the rocker pulleys 2204a,b provides a 2:1 block-tackle amplification on top of the lever arm advantage.

In some embodiments, the rocker bar system 2200 may further include first and second redirection pulleys 2208a and 2208b rotatably mounted to the shaft 1602. In at least one embodiment, as illustrated, the redirection pulleys 2208a,b may be rotatably mounted to the tail piece 1912, which is coupled to the shaft 1602. The first rocker pulley 2204a may be configured to receive the first drive cable 2114a from the first redirection pulley 2208a, and the second rocker pulley 2204b may receive the second drive cable 2114b from the second redirection pulley 2208b. In at least one embodiment, however, one or both of the redirection pulleys 2208a,b may be omitted from the rocker bar system 2200 and the drive cables 2114a,b may instead be fed directly to the first and second rocker pulleys 2204a,b, respectively, without departing from the scope of the disclosure.

Figure 22B:
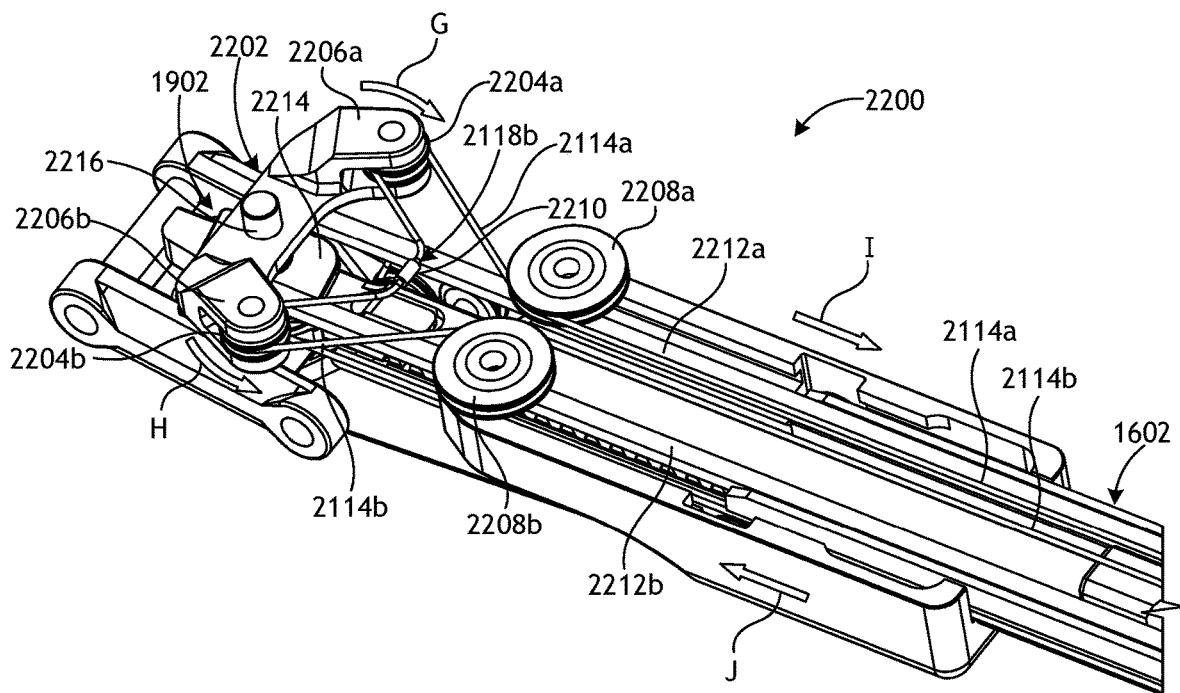
FIG. 22B is another enlarged, isometric side view of the rocker bar system of FIG. 22A.

FIG. 22B is another enlarged, isometric side view of the rocker bar system 2200, according to one or more embodiments. In FIG. 22B, the tail piece 1912 (FIG. 22A) and a portion of the shaft 1602 are omitted to enable viewing of various component parts of the rocker bar system 2200. As discussed above, the first drive cable 2114a may be received by the first redirection pulley 2208a, which redirects the first drive cable 2114a to the first rocker pulley 2204a, and the second drive cable 2114b may be received by the second redirection pulley 2208b, which redirects the second drive cable 2114b to the second rocker pulley 2204b.

In some embodiments, one or more additional pulleys (not shown) may be arranged between the redirection pulleys 2208a,b and the rocker pulleys 2204a,b, respectively. The additional pulleys may prove advantageous in creating an arc path for the cables 2114a,b, instead of following a straight line. The arc path(s) may be dimensioned to ensure a length conservative mechanism in the tail piece 1912 (FIG. 22A) that matches the cable management within the handle 1614 (FIG. 21). Alternatively, or in addition thereto, the lateral arms 2206a,b of the rocker bar 2202 may comprise rocker wheels (or half wheels), with respective cables 2114a,b running from opposite points on the diameter, around the arc of the rocker wheel down and to the corresponding redirection pulleys 2208a,b.

In some embodiments, as illustrated, the proximal ends 2118b of the drive cables 2114a,b may be coupled to each other, such as with a crimp 2210 or the like. In such embodiments, the crimp 2210 may be secured to the shaft 1602 and/or the tail piece 1912 (FIG. 21), thus anchoring the drive cables 2114a,b to the shaft 1602 at the proximal end 1902. In other embodiments, however, the proximal ends 2118b of the drive cables 2114a,b may alternatively be anchored and otherwise terminate at the lateral arms 2206a,b of the rocker bar 2202, without departing from the scope of the disclosure.

The cable management system 2200 may further include first and second drive rods 2212a and 2212b that extend longitudinally along the shaft 1602. The first drive rod 2212a may be pivotably coupled to the first lateral arm 2206a and the second drive rod 2212b may be pivotably coupled to the second lateral arm 2206b. The drive rods 2212a,b (alternately referred to as "articulation rods") may extend distally to the wrist 1606 (FIG. 16) where they may be operatively coupled to the wrist 1606 such that antagonistic longitudinal movement of the drive rods 2212a,b may cause the end effector (FIGS. 16-17) to articulate at the wrist 1606.

In some embodiments, as illustrated, the rocker bar 2202 may be rotatably mounted to a yoke 2214. The yoke 2214 may be secured to the proximal end 1902 of the shaft 1602 or may alternatively form an integral part thereof. The yoke 2214 may provide or define a pin 2216 and the rocker bar 2202 may be pivotably mounted to the yoke 2214 at the pin 2216. Accordingly, the rocker bar 2202 may be considered pivotably mounted to the proximal end 1902 of the shaft 1602.

Depending on the tension or tensile loading provided in the drive cables 2114a,b, the rocker bar 2202 may be urged to pivot about the pin 2216 in either a first angular direction, as indicated by the arrow G, or a second angular direction, as indicated by the arrow H, and opposite the first angular direction G. More specifically, operation of the actuation system 2100 (FIG. 21) in a first direction or mode (e.g., distal movement of the nut 2102 of FIG. 21) may apply tension on the first drive cable 2114a while simultaneously slackening the second drive cable 2114b. Such antagonistic operation of the drive cables 2114a,b may urge the rocker bar 2202 to pivot in the first angular direction G, which correspondingly moves (pushes) the first drive rod 2212a distally, as indicated by the arrow I, and simultaneously moves (pulls) the second drive rod 2212b proximally, as indicated by the arrow J. In contrast, operation of the actuation 2100 system in a second direction or mode (e.g., proximal movement of the nut 2102 of FIG. 21) may apply tension on the second drive cable 2114b while simultaneously slackening the first drive cable 2114. This may urge the rocker bar 2202 to pivot in the second angular direction H and correspondingly move (push) the second drive rod 2212b distally I and simultaneously move (pull) the first drive rod 2212a proximally J. Such antagonistic movement of the drive rods 2212a,b may cause the end effector (FIGS. 16-17) to articulate at the wrist 1606 (FIG. 16).

Figure 23:
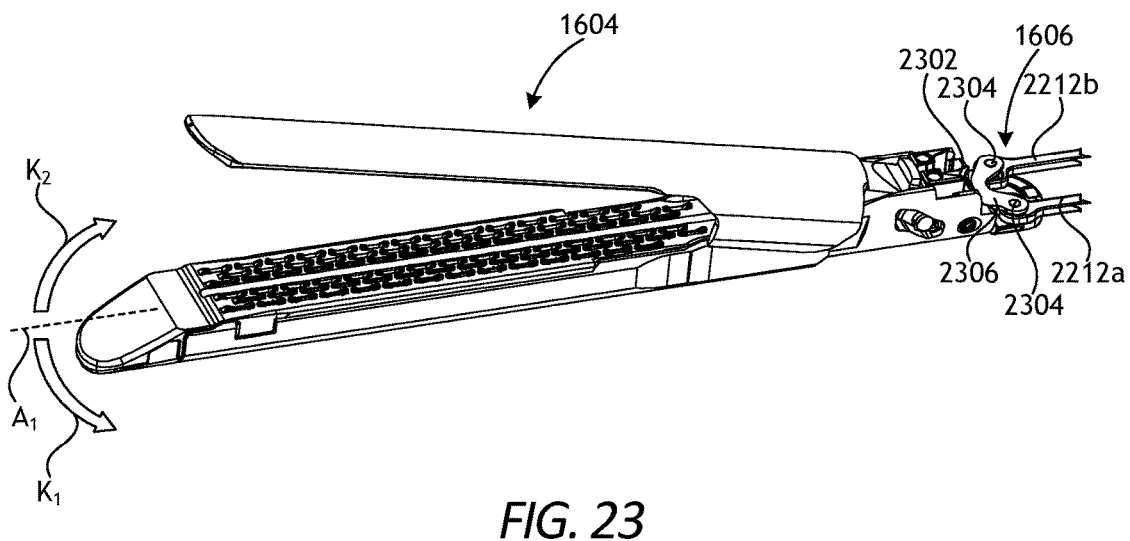
FIG. 23 is an enlarged isometric view of the end effector and an exposed view of the wrist of FIGS. 16-17, according to one or more embodiments.

Referring now to FIG. 23, with continued reference to FIGS. 22A-22B, depicted is an enlarged isometric view of the end effector 1604 and an exposed view of a portion of the wrist 1606, according to one or more embodiments. In FIG. 23, the body of the shaft 1602 has been removed to enable viewing of how the drive rods 2212a,b interconnect with or are otherwise operatively connected to the end effector 1604. In the illustrated embodiment, the end effector 1604 is mounted to an end effector mount 2302 that defines or otherwise provides two articulation pins 2304, and the distal end of each drive rod 2212a,b is rotatably mounted to a corresponding one of the articulation pins 2304. The drive rods 2212a,b are also interconnected at the distal ends via a distal link 2306, which together comprise a linkage configured to help articulate end effector mount 2302, and therefore the end effector 1604, in a plane parallel to the longitudinal axis $A_1$.

In this configuration, the drive rods 2212a,b translate antagonistically and parallel along the longitudinal axis $A_1$, such that as the first drive rod 2212a moves distally the second drive rod 2212b moves proximally, and vice versa, as generally discussed above. Moreover, distal movement of the first drive rod 2212a and simultaneous proximal movement of the second drive rod 2212b cooperatively act on the end effector mount 2302 to cause the end effector 1604 to rotate counter-clockwise, as indicated by the arrow $K_1$. In contrast, proximal movement of the first drive rod 2212a and simultaneous distal movement of the second drive rod 2212b cooperatively act on the end effector mount 2302 to cause the end effector 1604 to rotate clockwise, as indicated by the arrow $K_2$.

3. Implementing Systems and Terminology

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
   an elongate shaft extendable through a handle that provides a drive input;
   an actuation system housed within the handle and operatively coupled to the drive input such that actuation of the drive input operates the actuation system;
   a rocker bar system arranged at a proximal end of the shaft and actuatable to articulate an end effector at a distal end of the shaft, the rocker bar system further comprising a rocker bar pivotably mounted at the proximal end of the shaft; and first and second drive cables extending along a portion of the shaft, each drive cable having a proximal end anchored to the shaft proximal to the handle and a distal end anchored to the shaft distal to the handle, wherein the first and second drive cables are threaded through portions of the actuation and rocker bar systems such that operation of the actuation system acts on the first and second drive cables and thereby actuates the rocker bar system to articulate the end effector, and wherein antagonistic movement of the first and second drive cables caused by operation of the actuation system causes the rocker bar to pivot and thereby result in articulation of the end effector.

2. The robotic surgical tool of claim 1, further comprising an instrument driver arranged at an end of a robotic arm and matable with the handle, wherein the instrument driver provides a drive output matable with the drive input, and wherein the shaft extends through the instrument driver via a central aperture defined longitudinally through the instrument driver.

3. The robotic surgical tool of claim 1, wherein the actuation system comprises:
 a lead screw extending from the drive input and rotatable therewith;
 a nut threadably mounted to the lead screw such that rotation of the lead screw causes the nut to traverse the lead screw;
 a first pulley rotatably mounted to an armature extending laterally from the nut;
 a second pulley rotatably coupled to the handle and axially offset from the first pulley, wherein movement of the nut along the lead screw moves the first pulley toward or away from the second pulley; and
 first and second idler pulleys rotatably coupled to the handle and longitudinally spaced from each other,
 wherein the first drive cable is guided through the first and second pulleys and the first and second idler pulleys, and wherein the second drive cable is guided through the first and second pulleys.

4. The robotic surgical tool of claim 3, wherein the first idler pulley is mounted within the handle at or above a proximal end of external threading of the lead screw, and wherein the second idler pulley is mounted within the handle at or below a distal end of the external threading.

5. The robotic surgical tool of claim 3, wherein the nut defines one or more channel guides engageable with one or more opposing guide structures provided by the handle, and wherein receiving the one or more opposing guide structures in the one or more channel guides prevents the nut from rotating as the lead screw rotates.

6. The robotic surgical tool of claim 3, wherein proximal movement of one unit of length of the nut along the lead screw results in one or more units of length of the first drive cable being paid out from the actuation system to the shaft, and one or more units of length of the second drive cable being paid in to the actuation system from the shaft, and
 wherein distal movement of one unit of length of the nut along the lead screw results in one or more units of length of the second drive cable being paid out from the actuation system to the shaft, and one or more units of length of the first drive cable being paid in to the actuation system from the shaft.

7. The robotic surgical tool of claim 1, wherein the rocker bar system comprises:

first and second lateral arms provided on the rocker bar, wherein the first and second drive cables terminate at the rocker bar; and first and second drive rods pivotably coupled to the first and second lateral arms, respectively, and extending longitudinally to a wrist that interposes the distal end of the shaft and the end effector wherein pivoting movement of the rocker bar caused by antagonistic movement of the first and second drive cables causes the first and second drive rods to antagonistically operate at the wrist to thereby articulate the end effector.

8. The robotic surgical tool of claim 7, wherein the rocker bar system further comprises:
 a tail piece coupled to the proximal end of the shaft;
 first and second rocker pulleys rotatably mounted to the first and second lateral arms, respectively, and receiving the first and second drive cables, respectively;
 a first redirection pulley rotatably mounted to the tail piece and redirecting the first drive cable to the first rocker pulley; and
 a second redirection pulley rotatably mounted to the tail piece and redirecting the second drive cable to the second rocker pulley.

9. The robotic surgical tool of claim 8, further comprising:
 one or more first additional pulleys arranged between the first redirection pulley and the first rocker pulley; and
 one or more second additional pulleys arranged between the second redirection pulley and the second rocker pulley.

10. The robotic surgical tool of claim 7, wherein the rocker bar system further comprises a yoke coupled to the proximal end of the shaft, and wherein the rocker bar is pivotably mounted to the yoke at a pin defined by the yoke.

11. The robotic surgical tool of claim 1, wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, and any combination thereof.

12. A method of operating a robotic surgical tool, comprising:
 actuating a drive input of a robotic surgical tool, the robotic surgical tool having:
  an elongate shaft extending through a handle that provides the drive input;
  an actuation system housed within the handle and operatively coupled to the drive input;
  a rocker bar system arranged at a proximal end of the shaft; and
  first and second drive cables extending along a portion of the shaft and threaded through portions of the actuation and rocker bar systems, each drive cable having a proximal end anchored to the shaft proximal to the handle and a distal end anchored to the shaft distal to the handle;
 operating the actuation system by actuating the drive input and thereby antagonistically moving the first and second drive cables along the shaft;
 actuating the rocker bar system with the first and second drive cables and thereby antagonistically moving first and second drive rods extending to a wrist arranged at a distal end of the shaft; and
 articulating an end effector coupled to the wrist with antagonistic movement of the first and second drive rods.

13. The method of claim 12, wherein the handle is matable with an instrument driver arranged at an end of a robotic arm and the instrument driver provides a drive output, and wherein actuating the drive input comprises actuating the drive output mated with the drive input.

14. The method of claim 12, wherein the actuation system comprises a lead screw extending from the drive input, a nut threadably mounted to the lead screw, a first pulley rotatably mounted to an armature extending from the nut, a second pulley rotatably coupled to the handle and axially offset from the first pulley, and first and second idler pulleys rotatably coupled to the handle and longitudinally spaced from each other, and wherein operating the actuation system comprises:
  rotating the lead screw as the drive input rotates; and
  moving the nut along the lead screw as the lead screw rotates and thereby moving the first pulley toward or away from the second pulley,
  wherein the first drive cable is guided through the first and second pulleys and the first and second idler pulleys, and wherein the second drive cable is guided through the first and second pulleys.

15. The method of claim 14, further comprising:
  moving the nut proximally one unit of length along the lead screw and thereby paying out one or more units of length of the first drive cable from the actuation system to the shaft, and paying in one or more units of length of the second drive cable into the actuation system from the shaft; and
  moving the nut distally one unit of length along the lead screw and thereby paying out one or more units of length of the second drive cable from the actuation system to the shaft, and paying in one or more units of length of the first drive cable into the actuation system from the shaft.

16. The method of claim 12, wherein the rocker bar system includes a rocker bar pivotably mounted at the proximal end of the shaft and providing first and second lateral arms, the first and second drive rods being pivotably coupled to the first and second lateral arms, respectively and the first and second drive cables terminating at the rocker bar, and wherein antagonistically moving the first and second drive cables along the shaft comprises:
  pivoting the rocker bar and thereby antagonistically operating the first and second drive rods at the wrist; and
  articulating the end effector with antagonistic movement of the first and second drive rods.

17. The method of claim 12, further comprising moving the shaft relative to the handle while simultaneously articulating the end effector.

18. A robotic surgical tool, comprising:
  a shaft extended through a handle providing a drive input;
  an actuation system housed within the handle and having a lead screw extending from the drive input and a nut threadably mounted to the lead screw such that rotation of the lead screw causes the nut to traverse the lead screw;
  a rocker bar pivotably mounted at a proximal end of the shaft and having first and second drive rods pivotably coupled to first and second lateral arms, respectively, of the rocker bar and extending longitudinally to a wrist arranged at a distal end of the shaft; and
  first and second drive cables extending along a portion of the shaft, each drive cable having a proximal end anchored to the shaft proximal to the handle and a distal end anchored to the shaft distal to the handle,
  wherein the first and second drive cables are threaded through portions of the actuation system and the rocker bar such that movement of the nut along the lead screw acts on the first and second drive cables and correspondingly causes the rocker bar to pivot and antagonistically operate the first and second drive rods to articulate an end effector operatively coupled to the wrist.

19. The robotic surgical tool of claim 18, wherein the actuation system further includes:
  a first pulley rotatably mounted to an armature extending laterally from the nut;
  a second pulley rotatably coupled to the handle and axially offset from the first pulley, wherein movement of the nut along the lead screw moves the first pulley toward or away from the second pulley; and
  first and second idler pulleys rotatably coupled to the handle and longitudinally spaced from each other,
  wherein the first drive cable is guided through the first and second pulleys and the first and second idler pulleys, and wherein the second drive cable is guided through the first and second pulleys.

20. The robotic surgical tool of claim 19, wherein antagonistic movement of the first and second drive cables caused by operation of the actuation system causes the rocker bar to pivot and thereby antagonistically operate the first and second drive rods at the wrist to articulate the end effector.

* * * * *